United States Patent
Salmen et al.

[11] Patent Number: 6,140,130
[45] Date of Patent: Oct. 31, 2000

[54] DETECTION AND REMOVAL OF COPPER FROM WASTEWATER STREAMS FROM SEMICONDUCTOR AND PRINTED CIRCUIT BOARD PROCESSING

[75] Inventors: Kristine S. Salmen, Naperville; Angela S. Kowalski, Lisle; Brian V. Jenkins, LaGrange Park; John E. Hoots, St. Charles, all of Ill.

[73] Assignee: Nalco Chemical Company, Naperville, Ill.

[21] Appl. No.: 09/114,740

[22] Filed: Jul. 13, 1998

[51] Int. Cl.[7] ........................ G01N 21/64
[52] U.S. Cl. .............. 436/55; 210/709; 210/712; 210/729; 210/732; 210/736; 210/739; 422/62; 422/82.08; 436/80; 436/172
[58] Field of Search ............... 422/82.08, 62; 436/55, 80, 172; 210/662, 702, 709, 712, 729, 732, 735, 736, 739

[56] References Cited

U.S. PATENT DOCUMENTS

| | | |
|---|---|---|
| 3,877,878 | 4/1975 | Kerfoot et al. . |
| 3,898,042 | 8/1975 | Webb et al. . |
| 4,400,243 | 8/1983 | Ebdon et al. . |
| 4,462,913 | 7/1984 | Kim et al. . |
| 4,908,676 | 3/1990 | Bedell et al. . |
| 4,944,836 | 7/1990 | Beyer et al. . |
| 5,132,096 | 7/1992 | Hoots et al. . |
| 5,164,095 | 11/1992 | Sparapany et al. . |
| 5,278,074 | 1/1994 | Rao et al. . |
| 5,286,464 | 2/1994 | Dragisich . |
| 5,292,423 | 3/1994 | Wang . |
| 5,328,599 | 7/1994 | Seifert et al. . |
| 5,346,627 | 9/1994 | Siefert et al. . |
| 5,401,420 | 3/1995 | Siefert et al. . |
| 5,411,889 | 5/1995 | Hoots et al. . |
| 5,552,058 | 9/1996 | Fanning . |
| 5,578,829 | 11/1996 | Talasek et al. . |

FOREIGN PATENT DOCUMENTS

| | | |
|---|---|---|
| 195 12 908A1 | 10/1996 | Germany . |
| 96/38227 | 5/1996 | WIPO . |

OTHER PUBLICATIONS

Auyong et al., "On–Line Monitoring Of Toxic Materials in Sewage At The Lawrence Livermore Laboratory", U.S. Environ. Prot. Agency, issue EPA–600/9–81–018, pp. 199–206, (1981).

Ionics Inc. Inst. Div., "Water Quality Monitoring Guide For Anodic Stripping Voltammetry", date unknown.

Patterson, 2nd Edition, "Industrial Wastewater Technology", Chapter 7–Copper, pp. 91–109 (©1985 by Butterworth–Heinemann).

Kubiak et al., "Algae Columns With Anodic Stripping Voltammetric Detection", Anal. Chem., vol. 61, No. 5, pp. 468–471, (1989).

Glass et al., "Electrochemical Array Sensors For Plating Waste Stream Monitoring", Proc. AESF Annu. Tech. Conf., vol. 79, pp. 83–102 (1992).

(List continued on next page.)

*Primary Examiner*—Jan Ludlow
*Attorney, Agent, or Firm*—Maragert M. Brumm; Thomas M. Breininger

[57] ABSTRACT

A system and method for the detection and removal of copper from wastewater streams from semiconductor or printed circuit board manufacturing is described and claimed. The detection system and method involve the addition of a reagent that reacts with copper to quench the fluorophore present, with the decrease in fluorescence being detected by a fluorometer. The reduction of fluorescence is then used to calculate the amount of copper present in the form of Cu+2 ion in the wastewater. The removal system and method involve either the addition of a polymer that reacts with copper to form an insoluble precipitate with said precipitate then being removed by using any technique commonly known in the art; or the use of an ion exchange column to remove the copper from the wastewater stream.

14 Claims, 16 Drawing Sheets

OTHER PUBLICATIONS

Bratin et al., "On–Line Electrochemical Monitoring Of Waste and Rinse Water Streams", Proc. AESF. Annu. Tech. Conf., vol. 82, pp. 755–764 (1995).

Vanhumbeek, "Automatic Monitoring Of Copper In Waste Water From Plating Shops", Wat. Sci. Tech, vol. 13, pp. 539–544 (1981).

Connolly et al., "Instruments, On–Line Measurement of Sub–PPB Levels Of Metals Using X–Ray Fluorescence", Ultrapure Water, vol. 15, pp. 53–58 (1998).

Schlager, "On–Line Spectroscopic Monitoring Of Metal Ions For Environmental And Space Applications Using Photodiode Array Spectrometry", SPIE Optical Spec. Inst. and Tech., vol. 1318, pp. 220–233 (1990).

Beauchemin et al., "Determination Of Trace Metals In Reference Water Standards By Inductively Coupled Plasma Mass Spectrometry With On–Line Preconcentration", Anal. Chem., vol. 61, pp. 1857–1862 (1989).

Cnobloch, "Continuous Monitoring Of Heavy Metals In Industrial Waste Waters", Analytica Chemica Acta, vol. 114, pp. 303–310 (1980).

Product Literature From Environmental Technologies Group, Inc. About "ETG Metalyzer™ 5000" (1995).

Ng et al.., "Quartz Crystal Microbalance Sensor Deposited With Langmuir–Blodgett Films Of Functionalized Polythiophenes And Application To Heavy Metal Ions Analysis", vol. 14, pp. 1748–1752 (1998).

Groves et al., "Inductively Coupled Plasma Monitoring Of Semi–Conductor Wastewater", Process Control and Quality, vol. 7, pp. 85–90 (1995).

"The Filtration Spectrum", from Osmonics, Inc., date unknown.

"Water Treatmemt Membrane Processes", edited by Joel Malleviallie et al., ©1996 McGraw–Hill, pp. 3.3–3.4, 3.12–3.13, 3.12, ISBN 0–07–001559–7.

"Membrane Separation Processes", edited by Patrick Meares, ©1976 by Elsevier Scientific Publishing Company, Amsterdam, pp. 512–513.

"Carbon Adsorption Handbook", edited by Cheremisinoff and Ellerbusch, ©1978 by Ann Arbor Science Publishers, Inc., pp. 307–310.

Vanhumbeeck et al., paper on "Automatic Analyser For Copper In Waste Water From Plating Shops", pp. 1–7, source and date unknown.

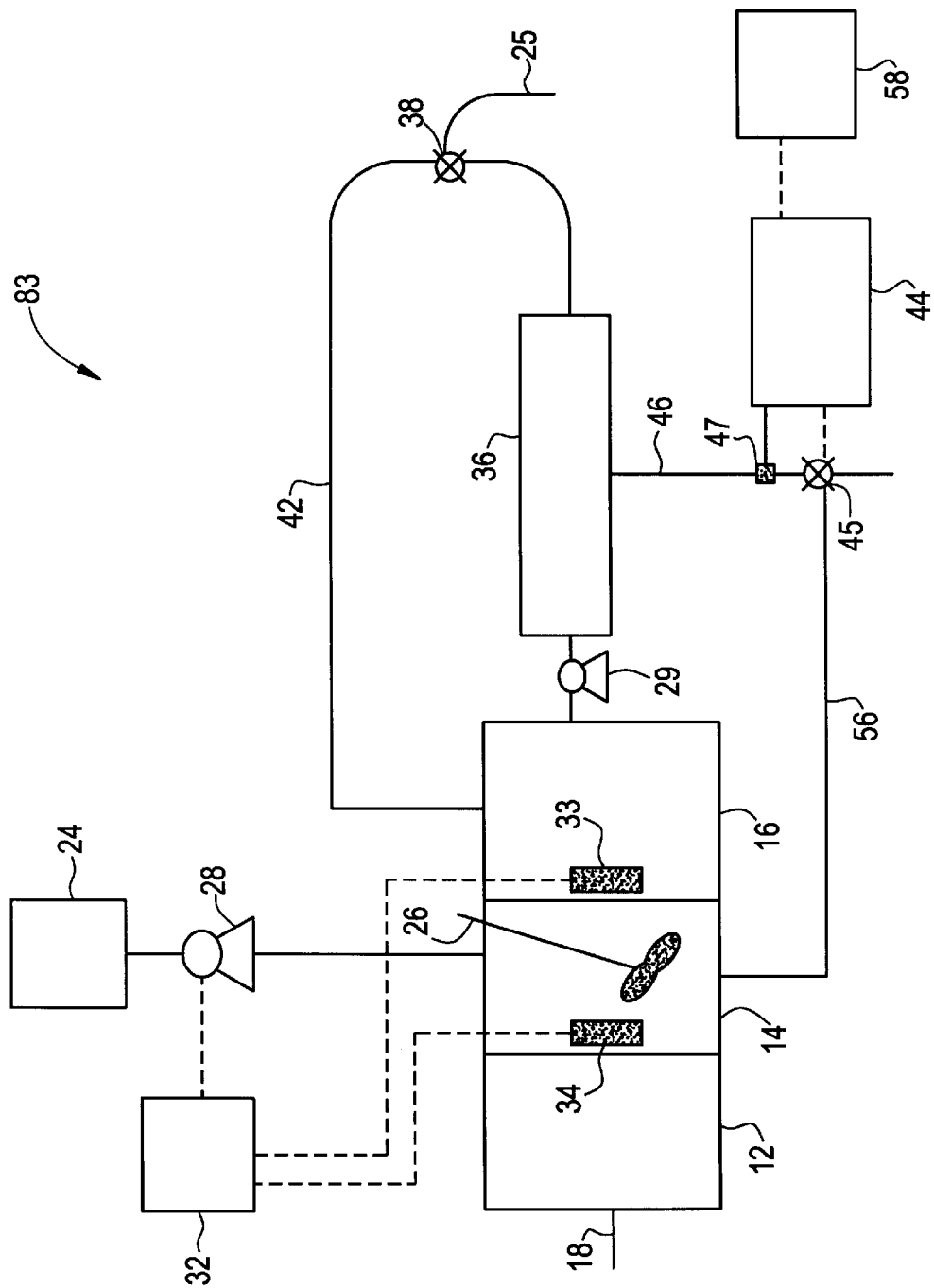

DETECTION AND REMOVAL OF COPPER FROM WASTEWATER STREAMS FROM SEMICONDUCTOR AND PRINTED CIRCUIT BOARD PROCESSING

FIELD OF THE INVENTION

This invention relates to the art of detection and removal of metal from wastewater streams. Specifically the invention relates to the detection and removal of copper from wastewater streams from semiconductor and printed circuit board processes.

BACKGROUND OF THE INVENTION

Until the development of copper interconnect technology, copper was not found in wastewater from the production of multilayer microchips by the semiconductor industry. Copper is now being used as a replacement for aluminum and/or tungsten because of its lower electrical resistivity in processes referred to as chemical-mechanical polishing or chemical-mechanical planarization (known as "CMP") and therefore is now being found in wastewater. Copper is an undesirable component of wastewater because of its toxicity to aquatic organisms such as fish and adverse health effects to humans who ingest copper-contaminated drinking water. Thus, copper is regulated in discharges to the environment so it is imperative that viable methods be found to detect and remove copper in wastewater streams from the semiconductor industry.

For purposes of this application, printed circuit boards, also known as printed wiring boards, are defined as "physical structures on which electronic components such as semiconductors and capacitors are mounted". In contrast to the semiconductor industry, copper is usually found in the wastewater from the printed circuit board industry. However, methods to detect and remove copper from the wastewater of the printed circuit board industry have not yet been optimized.

Analytical methods useful to detect copper are described in the following references:

U.S. Pat. No. 5,132,096 claims an on-stream analyzer to determine the concentration of a treating agent added to a body of water, and to determine the presence of an uncompensated stress metal which may be present in spite of the treating agent. The use of an unconsumable transition metal tracer is described with this analyzer.

U.S. Pat. No. 5,278,074 claims a method for controlling the concentration of an aromatic azole corrosion inhibitor in the water of an industrial aqueous system.

U.S. Pat. No. 5,411,889 claims a method of regulating the in-system concentration of a water treatment agent in an industrial fluid system comprising: adding an inert tracer to an industrial fluid system, the inert tracer being added in known proportion to a target specie also being added to said industrial fluid system wherein the system consumption of the target specie is effected by the water treatment agent; drawing a sample of fluid from said industrial fluid system; monitoring the target-specie by analysis of said sample to determine at least one characteristic that can be correlated to an in-system concentration of said target-specie; monitoring said inert tracer by analysis of said sample to determine the in-system concentration of said inert tracer; determining the system consumption of the target specie from the measured in-system concentration of the target specie and the inert tracer; and regulating the in-system concentration of the water treatment agent in the fluid system based on the system consumption of the target specie. Example 3 (Columns 31–32) describes using the process to detect cupric ion ($Cu^{+2}$) in a series of synthetic industrial water solutions.

U.S. Pat. No. 3,877,878 discloses an analytical device and a method for monitoring heavy metals in natural waters.

U.S. Pat. No. 3,898,042 discloses a method and apparatus for continuously determining total copper in an aqueous stream.

U.S. Pat. No. 4,908,676 discloses sensors for detecting dissolved substances, including copper, in aqueous fluids.

U.S. Pat. No. 4,400,243 discloses the monitoring of the heavy metal ions silver, cadmium, lead and copper using an electrode system.

U.S. Pat. No. 5,292,423 discloses an apparatus and a method to use the apparatus to analyze trace metals, including copper.

U.S. Pat. No. 5,578,829 discloses a method of monitoring a material flow for a contaminant therein.

German Patent 19512908 discloses a method for analyzing wastewater from galvanizing wastewaters.

Additional references describing detecting methods for copper include the following: Ionics Inc. Instrument Division, "Water Quality Monitoring Guide for Anodic Stripping Voltammetry"; "Industrial Wastewater Treatment Technology", $2^{nd}$ Edition, James W. Patterson ©1985 by Butterworth-Heinemann, "Chapter 7-Copper, pp. 91–109; Auyong, "On-Line Monitoring of Toxic Materials in Sewage at the Lawrence Livermore Laboratory", U.S. Environmental Protection Agency, issue EPA-600/9-81-018, 1981; Kubiak and Wang, "Algae Columns with Anodic Stripping Voaltammetric Detection", Anal. Chem., vol. 61, no. 5, Mar. 1, 1989, pp. 468–471; Glass et al., "Electrochemical Array Sensors For Plating Waste Stream Monitoring", Proc. AESF Annu. Tech. Conf., vol. 79, pp. 83–102 (1992); Bratin et al., "On-Line Electrochemical Monitoring of Waste and Rinse Water Streams", Proc. AESF. Annu. Tech. Conf., vol. 82, pp. 755–764 (1995); Vanhumbeek, "Automatic Monitoring of Copper in Waste Water From Plating Shops", Wat. Sci. Tech., Vol. 13, pp.539–544 (1981); Connolly et al., "On-Line Measurement of Sub-PPB Levels of Metals Using X-Ray Fluorescence", Ultrapure Water, vol. 15, pp. 53–58 (1998); Schlager, "On-Line Spectroscopic Monitoring of Metal Ions For Environmental and Space Applications Using Photodiode Array Spectrometry"; Beauchemin et al., "Determination of Trace Metals in Reference Water Standards by Inductively Coupled Plasma Mass Spectrometry with On-Line Preconcentration", Anal. Chem., vol. 61 pp. 1857–1862 (1989); Cnobloch, "Continuous Monitoring of Heavy Metals In Industrial Waste Waters", Analytica Chemica Acta, vol. 114, pp. 303–310 (1980); Product Literature from Environmental Technologies Group, Inc. about "ETG METALYZER™ 5000"; Ng et al., "Quartz Crystal Microbalance Sensor Deposited with Langmuir-Blodgett Films of Functionalized Polythiophenes and Application to Heavy Metal Ions Analysis", Langmuir, vol. 14, pp. 1748–1752 (1998); and Groves et al., "Inductively Coupled Plasma Monitoring of Semi-conductor Wastewater", Process Control and Quality, vol. 7, pp. 85–90 (1995).

Methods useful to remove copper from aqueous systems are described in the following references:

U.S. Pat. No. 4,462,913 discloses a process for treating wastewater, produced in wire drawing and rolling, with said wastewater containing fat and heavy metal ions, including copper.

U.S. Pat. No. 5,164,095 discloses dithiocarbamate polymers and use of these polymers in removing heavy metals from water.

U.S. Pat. No. 5,346,627 discloses a method for removing monovalent and divalent metals including copper from a fluid stream using a water soluble ethylene dichloride ammonia polymer having a molecular weight of from 500 to 100,000 that contains from 5 to 50 mole percent of dithiocarbamate salt groups to form complexes with the monovalent and divalent metals.

U.S. Pat. No. 5,328,599 claims a wastewater treatment system and method for chemical precipitation and removal of metals from wastewater in a continuous or batch treatment process which includes an ion-selective electrode and a reference electrode disposed in a precipitation tank for measuring an electrochemical potential therebetween in a predetermined range. A controller unit is provided which is responsive to the electrochemical potential in the predetermined range and is connected to a precipitant feed unit for automatically controlling the chemical precipitant fed into the precipitation unit.

U.S. Pat. No. 5,401,420 claims a method of automatically controlling the chemical feed of an organic sulfide chemical precipitant to a wastewater treatment system. The organic sulfide is selected from the group consisting of dithiocarbamates, trimercaptotriazines, trithiocarbonates and polymeric dithiocarbamates.

U.S. Pat. No. 5,286,464 discloses that lead and cadmium ions are selectively removed and reclaimed from aqueous liquids containing the ions of these metals using an ion exchange resin which comprises a modified silica gel. It claims: in an ion exchange process to selectively remove the metals, lead and cadmium, from aqueous liquids containing the ions of these metals wherein these liquids are contacted with an ion exchange resin for a period of time sufficient for the ion exchange resin to complex with the lead and cadmium ions in the aqueous liquids and then regenerating the resin to remove and recover the metals from the resin; the improvement which comprises using as the ion exchange resin an amorphous silica gel having a surface area of at least 100M$^2$/g having at least 10% of its surface silanol groups reacted with a triethoxy silane selected from the group consisting of Bis(2-hydroxyethyl)-3-aminopropyltriethoxysilane and N-[3-(triethoxysilyl)propyl]-4,5-dihydroimidazole.

U.S. Pat. No. 5,552,058 discloses a filtering method for removing particulate matter and dissolved heavy metals from cooling tower water by passing the cooling tower water through a filter assembly containing a particulate matter filter and a heavy metals filter having a filter element having metal particles bound together in a porous sponge like structure.

PCT WO 96/38227 discloses and claims water-soluble polymers for recovery of metals from solids.

Relative size of various common materials used in filtration is described in "The Filtration Spectrum" from Osmonics, Inc., 5951 Clearwater Drive, Minnetonka, Minn. 55343.

Solid-Liquid separation various techniques are described in Chapter 3.1 of the book, "Water Treatment Membrane Processes", edited by Joel Malleviale et al., ©1996 McGraw-Hill, pp. 3.3–3.4, 3.12–3.13, 3.12ISBN 0-07-001559-7. Solid-Liquid separation using ultrafiltration can be found in the same reference at pp. 10.1, 10.12 and 10.8. Solid-Liquid separation using microfiltration can be found in the same reference at pp. 11.1 and 11.3–11.5. Solid-Liquid separation using electrodialysis can be found in the same reference at pp. 12.1–12.10.

Membrane Separation Processes are described in "Membrane Separation Processes", edited by Patrick Meares, ©1976 by Elsevier Scientific Publishing Company, Amsterdam, pp. 512–513. They are also described in "Membrane Handbook", edited by W. S. Winston Ho, ©1992 by Van Norstrand Reinhold, pp. 326–327, 335–336, 348–354.

"Carbon Adsorption Handbook" edited by Cheremisinoff and Ellerbush, ©1978 by Ann Arbor Science Publishers, Inc., describes the removal of copper(II) by activated carbon using synthetic seawater of high ionic strength. Among the six different kinds of activated carbon tested, Barneby-Cheney PC-8592 was the most efficient adsorbent for Cu(II) removal (adsorption). However, the removal efficiency was still very poor with a low 6% (FIGS. 8–10).

What is needed is a method to both detect and remove copper from wastewater process streams from the manufacture of semiconductors and printed circuit boards that is reliable under actual manufacturing conditions. This method must be capable of automation and allow for upsets in process conditions.

SUMMARY OF THE INVENTION

The first aspect of the invention is a system to detect and remove copper from wastewater streams in the manufacture of semiconductors comprising:

a) a fluorometer;

b) a reagent that when added to the wastewater reacts with any copper present in the form of $Cu^{+2}$ ion to quench the fluorescence of said reagent;

c) a polymer, which when added to the wastewater stream causes the precipitation of any copper present in the form of $Cu^{+2}$ ion;

d) a polymer distribution and reaction component comprising
  i) a means to add polymer to the wastewater,
  ii) a controller to regulate the flow of polymer into the wastewater, and
  iii) at least two tanks;

e) at least one sensor to detect unreacted polymer; and f) a means to separate the precipitate from the wastewater stream; and g) optionally a reagent to adjust pH of wastewater prior to it being contacted with polymer; and h) optionally, at least one tank to hold the wastewater while its pH is being adjusted; and i) optionally, at least one tank to bold the wastewater while it is being equalized, prior to its pH being adjusted.

The second aspect of this invention is a system to detect and remove copper from wastewater streams in the manufacture of printed circuit boards comprising:

a) a fluorometer;

b) a reagent that when added to the wastewater reacts with any copper present in the form of $Cu^{+2}$ ion to quench the fluorescence of said reagent;

c) a polymer, which when added to the wastewater stream causes the precipitation of any copper present in the form of $Cu^{+2}$ ion;

d) a polymer distribution and reaction component comprising
  i) a means to add polymer to the wastewater,
  ii) a controller to regulate the flow of polymer into the wastewater, and iii) at least two tanks;
e) at least one sensor to detect unreacted polymer; and
f) a means to separate the precipitate from the wastewater stream; and
g) optionally a reagent to adjust pH of wastewater prior to it being contacted with polymer; and
h) optionally, at least one tank to hold the wastewater while its pH is being adjusted; and
i) optionally, at least one tank to hold the wastewater while it is being equalized, prior to its pH being adjusted.

The third aspect of this invention is a method to detect and remove copper from wastewater streams from semiconductor processes comprising:

using a fluorometer and a fluorometric analytical method for the detection of copper,
using a polymer to react with said copper in the form of $Cu^{+2}$ ion to form a precipitate, and
removing said precipitate from said wastewater.

The fourth aspect of this invention is a method to detect and remove copper from wastewater streams from printed circuit board processes comprising:

using a fluorometer and a fluorometric analytical method for the detection of copper,
using a polymer to react with said copper in the form of $Cu^{+2}$ ion to form a precipitate, and
removing said precipitate from said wastewater.

The fifth aspect of the invention is a system to detect and remove copper from wastewater streams in the manufacture of semiconductors comprising:

a) a fluorometer;
b) a reagent that when added to the wastewater reacts with any copper present in the form of $Cu^{+2}$ ion to quench the fluorescence of said reagent;
c) at least one ion exchange column; and
d) optionally, a tank to contain the wastewater when it is being equalized.

The sixth aspect of this invention is a system to detect and remove copper from wastewater streams in the manufacture of printed circuit boards comprising:

a) a fluorometer;
b) a reagent that when added to the wastewater reacts with any copper present in the form of $Cu^{+2}$ ion to quench the fluorescence of said reagent;
c) at least one ion exchange column; and
d) optionally, a tank to contain the wastewater when it is being equalized.

The seventh aspect of this invention is a method to detect and remove copper from wastewater streams from semiconductor processes comprising:

using a fluorometer and a fluorometric analytical method for the detection of copper, and
using at least one ion exchange column to remove copper from said wastewater.

The eighth aspect of this invention is a method to detect and remove copper from wastewater streams from printed circuit board processes comprising:

using a fluorometer and a fluorometric analytical method for the detection of copper,
using at least one ion exchange column to remove copper from said wastewater.

BRIEF DESCRIPTION OF THE DRAWINGS

Throughout this application, dotted lines on the figures are meant to depict electrical signal connections between the indicated pieces of equipment.

FIG. 8B is the same as FIG. 1A except that a second sensor for unreacted polymer is used in the third tank of the 3-tank polymer addition and reaction tank system. Both sensors are connected to the controller used to determine the amount of polymer added to the wastewater stream.

DESCRIPTION OF THE INVENTION

For purposes of this application, a fluorophore is any moiety that when excited with light of an appropriate wavelength will emit light at a longer wavelength than the excitation light and this emission light is then capable of being detected by a fluorometer.

For purposes of this application CMP stands for "chemical-mechanical polishing or chemical-metal planarization". The CMP process, which involves removal of both dielectric and metal surface layers from a wafer, is described in great detail in U.S. Pat. No. 4,944,836. Wastewater from the metal-CMP process contains used polishing slurry, with this used polishing slurry being composed of oxidant, abrasives, which include, but are not limited to, silica, alumina, manganese oxide and tungsten oxide, chelants including, but not limited to, citrate and ammonia, metals, including, but not limited to, copper, in the form of $Cu^{+2}$ ion, which is sometimes referred to as soluble copper, and other organic and inorganic additives including, but not limited to, surfactants; and rinse water. Acids and/or bases used for pH adjusting may also be present.

It is noted that oxidants are typically present in wastewater from CMP semiconductor processes. It is known that prior to removal of copper from the wastewater it is desirable to remove any oxidants present. This is because if the oxidants are present in the wastewater contacted with the polymer, as is described in the current invention, the oxidants will react with the polymer first, causing degradation of the polymer before it gets a chance to react with the copper. This degradation is undesirable as it means additional quantities of polymer are required to react with the copper present in the form of $Cu^{+2}$ ion. Also oxidants present in wastewater will degrade ion exchange resins and certain synthetic membranes in microfilters. A technique known in the art for destroying these oxidants is to add sodium bisulfite or sodium sulfite in a wastewater pretreatement process. The removal of oxidants from the wastewater from a semiconductor process is not part of the instant invention. Nevertheless, the wastewater that copper will be removed from as described herein is assumed to have all of its oxidants destroyed prior to having its copper removed.

Wastewater from manufacture of printed circuit boards does not contain abrasive solids, but does contain organic and inorganic components, including, but not limited to, etchants, photopolymer developers, resist materials, photopolymer strippers, acids, and bases; metals, including, but not limited to, copper; and rinse water.

Figure 1:
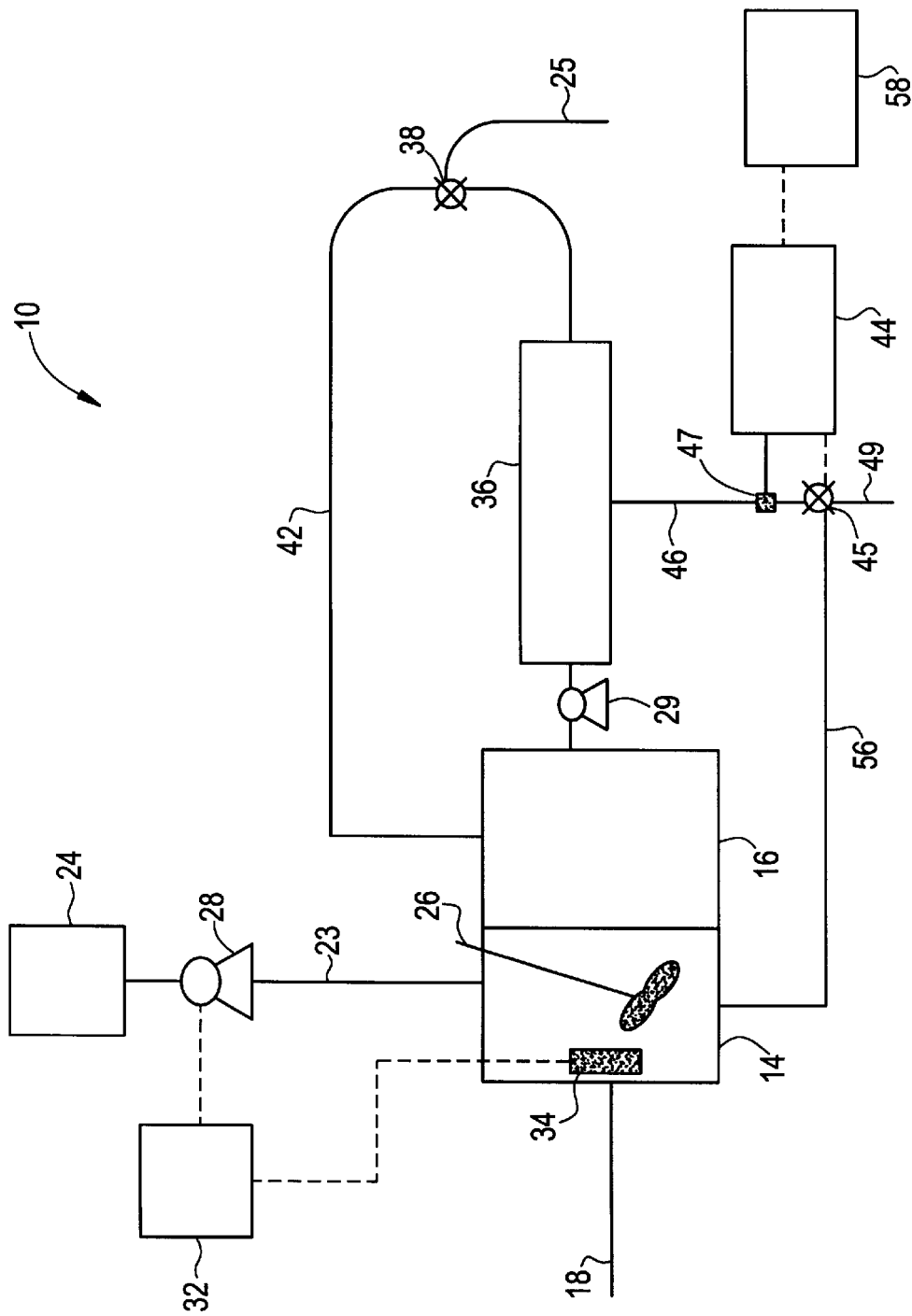
FIG. 1 depicts a wastewater treatment system comprising a two-tank polymer addition/reaction system and a fluorometric method of detecting copper in the wastewater after the wastewater has been treated with polymer. A microfilter is used to separate the polymer-copper precipitate and other solids present from the wastewater stream. In this figure the sensor for detection of unreacted polymer is positioned in the first tank of the two tank system used for addition and reaction of the polymer with said wastewater. The signal from the fluorometer is used to control a valve in a feed forward manner by opening it to send treated wastewater to disposal or in the event unacceptably high levels of copper are detected in the treated wastewater, the valve will be automatically closed to send the treated wastewater back for further processing.

Referring now to FIG. 1, copper detection and removal system 10 is illustrated. Copper detection and removal system 10 has two tanks, first tank 14 and second tank 16. Inlet line 18 supplies wastewater from either a CMP process or a process to make printed circuit boards to first tank 14. The pH of the wastewater is measured and, if necessary, adjusted by addition of a suitable reagent such as sodium hydroxide to make basic or sulfuric acid to make acidic, so that the pH is between about 5 and about 10. After ascertaining that the pH of said wastewater is in the proper range, polymer is added from polymer storage area 24 using a suitable conveying means, such as pump 28, through polymer feed line 23.

The polymer is added to first tank 14 with stirring from stirring implement 26. The polymer used can be any suitable polymer capable of reacting with dissolved copper to form a suitable precipitate. Throughout this application it is understood that copper in wastewater streams from semiconductor and printed circuit board processes is usually present in the form of $Cu^{+2}$ ion which complexes with other components of said wastewater. These other components include, but are not limited to, EDTA (ethylenediaminetetraacetic acid), water, acids and acid salts. Therefore, when wastewater is contacted with either polymer or suitable reagent it is the $Cu^{+2}$ ion that actually reacts with said polymer or suitable reagent, not copper metal itself.

Suitable polymers are water soluble ethylene dichloride ammonia polymers that contain at least 5 mole % of dithiocarbamate salt groups as described in U.S. Pat. No. 5,346,627, herein incorporated by reference. The preferred polymer is a water soluble ethylene dichloride ammonia polymer having a molecular weight from 500 to 100,000 that contains from 5 to 50 mole percent of dithiocarbamate salt groups. The more preferred polymers are NALMET® 8702 (which contains approximately 33% of dithiocarbamate salt groups) and NALMET® 1689 (which contains approximately 50% of dithiocarbamate salt groups. The most preferred polymer is NALMET® 1689. All NALMET® polymers are available from Nalco Chemical Company, One Nalco Center, Naperville, Ill. 60563-1198, (630) 305-1000. The amount of polymer added to first tank 14 is controlled by controller 32. A suitable controller is commercially available and sold under the trademark NALMET® 2000 by Nalco Chemical Company, Controller 32 is linked to sensor 34 which is placed in first tank 14. Sensor 34 detects unreacted polymer in first tank 14 and adjusts the flow of polymer by adjusting the pumping rate of pump 28, such that the level of unreacted polymer is kept to a minimum. A description of sensor 34 can be found in U.S. Pat. Nos. 5,401,420; 5,328,599 and 5,411,889, which are all herein incorporated by reference.

Wastewater leaves first tank 14 and enters second tank 16 where it is concentrated to increase the level of solids present by being mixed with rejected stream 42. Rejected stream 42 contains rejected water with solids. The wastewater in second tank 16 now contains solids up to a level of about 10%. This wastewater-solids mixture is then conveyed to microfilter 36 using pump 29 as the means of conveyance. In microfilter 36, solids, which include precipitated polymer-$Cu^{+2}$ as well as other solids present in the wastewater are separated from water. The solids circulate, along with some water, to valve 38 where a certain amount of solids exit in sludge line 25. Sludge line 25 is then sent out for either disposal in an environmentally sound manner or for further processing such as dewatering, not depicted, to recover copper (and/or other materials) prior to disposal. As stated previously, reject stream 42 contains rejected water with up to about 10% solids.

Treated wastewater exits microfilter 36 as permeate stream 46. Fluorometer 44 is positioned to remove a sample from permeate stream 46 at sample point 47. Fluorometers suitable for use in this system are known in the art and are commercially available from Turner Designs Inc., 845 West Maude Avenue, Sunnyvale, Calif., 94086. The sample of permeate is then contacted with a suitable reagent. The suitable reagent is chosen such that it is fluorescent, but when it reacts with $Cu^{+2}$ it forms a reagent-$Cu^{+2}$ moiety that has less fluorescence than that of the reagent by itself. The amount of quenching of the fluorescence of the suitable reagent is directly related to the amount of copper that is present in the sample. Suitable reagents to react with $Cu^{+2}$ are bicinchoninate organic compounds, which are described in U.S. Pat. No. 5,411,889, which is incorporated by reference. In addition to those reagents described in U.S. Pat. No. 5,411,889, the composition of another reagent suitable to react with $Cu^{+2}$ ion is glycine (10.2%), 1,10-phenanthroline (0.070%), then adjust pH with aqueous 6N HCl to a pH of 3.0±0.1, $Zn(SO_4) \cdot 7H_2O$ (0.043% ) and water (85.6%, includes water added from all sources, including 6 N HCl).). The mechanism by which this method works to detect copper is believed to be, without intending to be bound thereby, as follows: when either the reagents described in U.S. Pat. No. 5,411,889 or the zinc-(1,10-phenanthroline) reagent described above come in contact with $Cu^{+2}$, a reagent-$Cu^{+2}$ moiety (which may be, but does not have to be, a complex) is formed and the fluorescence of the reagent-$Cu+^2$ moiety is lower than the fluorescence of the original suitable reagent. As the level of $Cu^{+2}$ increases, the level of fluorescence decreases (i.e., reverse fluorescence method). In summary, with suitable fluorescent reagents, when they are combined with $Cu^{+2}$ the formation of the suitable reagent-$Cu^{+2}$ moiety causes a decrease in fluorescence which is linearly related to the level of $Cu^{+2}$ present.

The change in fluorescence observed can be used to determine the amount of copper still present in permeate stream 46, according to the method described in U.S. Pat. No. 5,411,889, previously incorporated by reference. Should the amount of copper detected exceed specifications, then permeate stream 46 can be recirculated through recirculation line 56 back to first tank 14 for further treatment with polymer. This recirculation can be done automatically by having a signal from fluorometer 44 used to control drain valve 45 as follows: the normal position of drain valve 45 is open, leading permeate stream 46 to disposal line 49. However, when the copper level is found by fluorometric analysis to be past an acceptable setpoint, then the signal from fluorometer 44 is used to close drain valve 45 which causes permeate stream 46 to recirculate back in recycle line 56 to first tank 14 for further treatment with polymer. Optional datalogger 58 can be used to keep a continuous record of fluorescence detected so that the overall removal process can be constantly monitored.

Figure 1A:
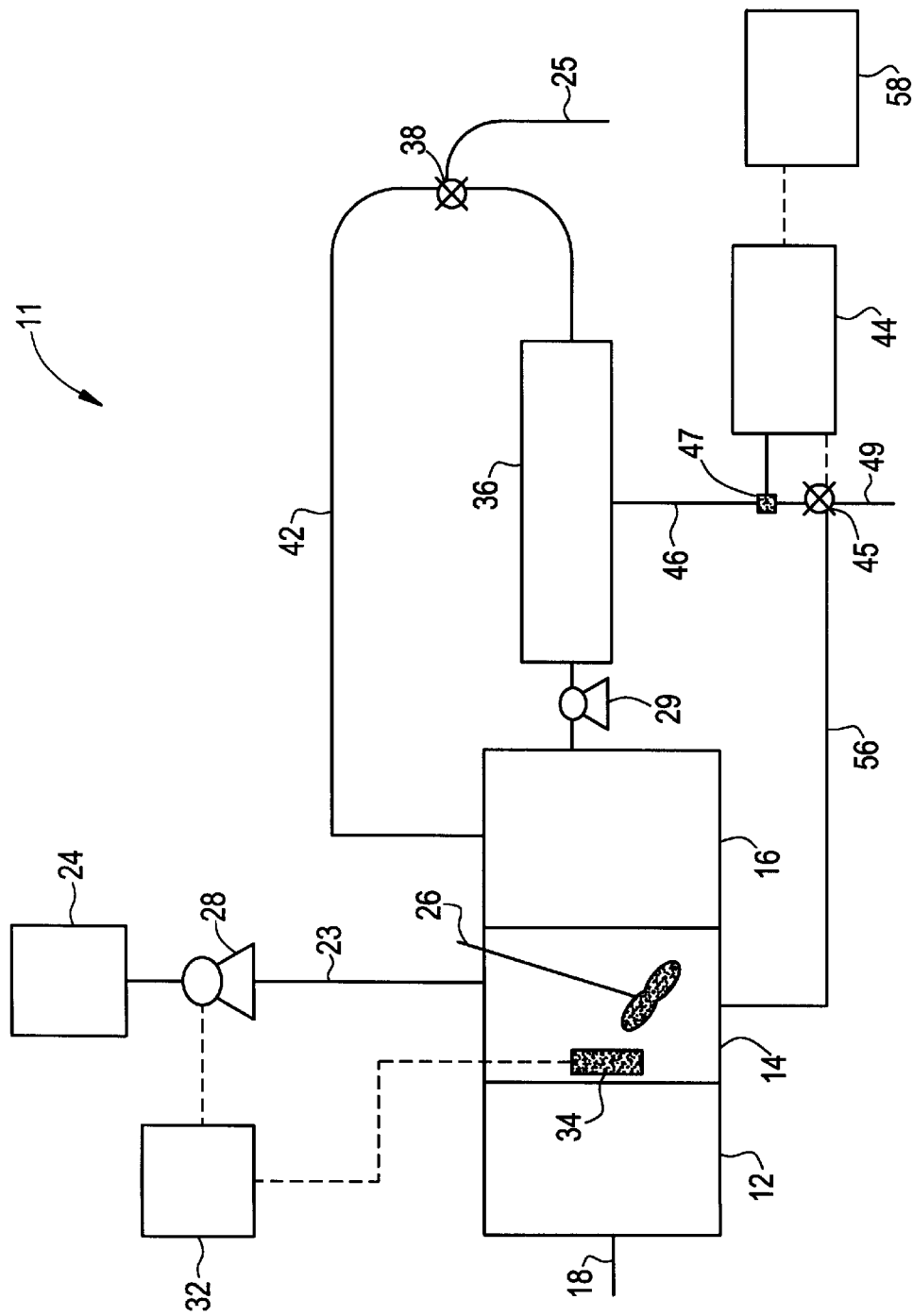
FIG. 1A depicts a wastewater treatment system comprising a three-tank polymer addition system and a fluorometric method of detecting copper in the wastewater after the wastewater has been treated with polymer. A microfilter is used to separate the polymer-copper precipitate and other solids present from the wastewater stream. There are three tanks present in this system, with the first tank being used to adjust the pH of the wastewater prior to the wastewater being contacted with the polymer. In this figure the sensor for detection of unreacted polymer is positioned in the second tank of the three tank system used for addition and reaction of the polymer with said wastewater. The signal from the fluorometer is used to control the distribution of treated wastewater in a feed forward manner the same as in FIG. 1.

FIG. 1A depicts copper detection and removal system 11. FIG. 1A is the same as copper detection and removal system 10, as illustrated in FIG. 1, except that optional tank 12 is present in said system 11. Optional tank 12 is the tank into which wastewater first enters. The pH of wastewater is adjusted to be between about 5 and about 10 in optional tank 12 using a suitable reagent described previously. From optional tank 12, wastewater is conveyed to first tank 14 wherein treatment with polymer occurs. As is the case with system 10, sensor 34 is positioned in first tank 14.

Figure 2:
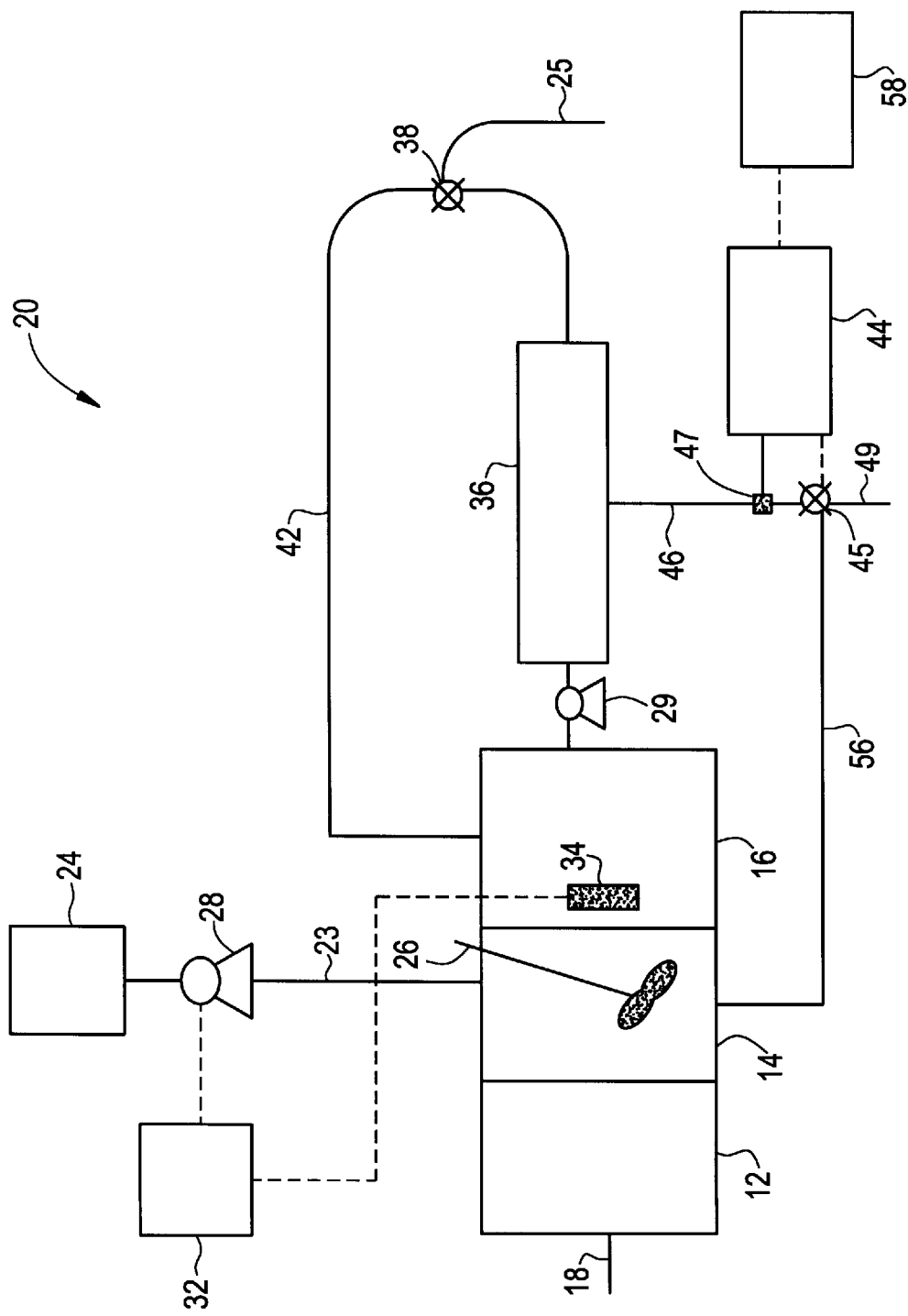
FIG. 2 depicts a wastewater treatment system comprising a polymer addition system and a fluorometric method of detecting copper in the wastewater after the wastewater has been treated with polymer. A microfilter is used to separate the polymer-copper precipitate and other solids present from the wastewater stream. In this figure the sensor for detection of unreacted polymer is positioned in the third tank of the three tank system for addition and reaction of the polymer with said wastewater. The signal from the fluorometer is used to control the distribution of treated wastewater in a feed forward manner the same as in FIG. 1.

FIG. 2 depicts copper detection and removal system 20. Copper detection and removal system 20 is the same as copper detection and removal system 11, except that sensor 34 is positioned in second tank 16, rather than in first tank 14. Sensor 34 is still designed to detect unreacted polymer, with the amount of unreacted polymer being used to control pump 28.

Figure 3:
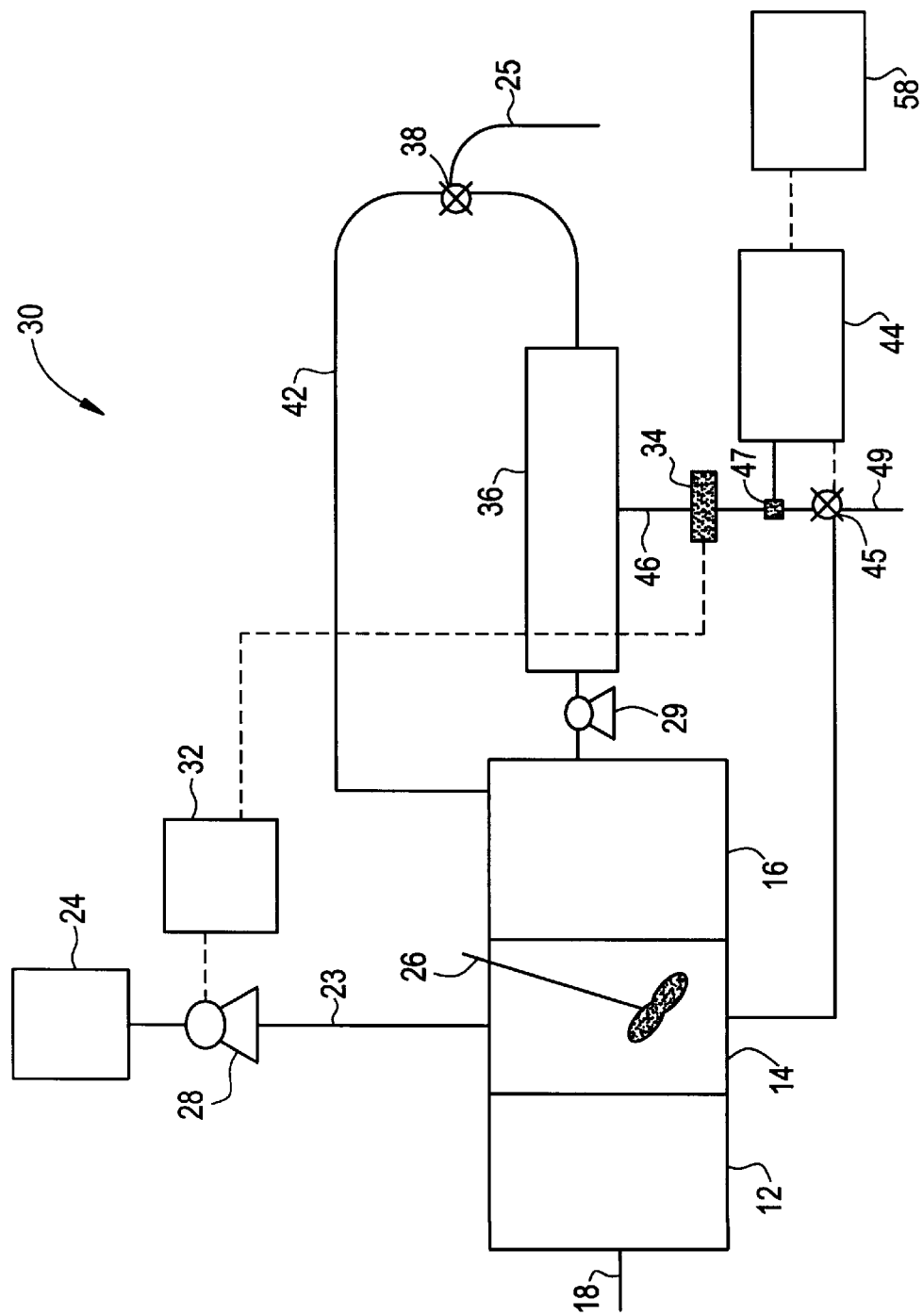
FIG. 3 depicts a wastewater treatment system comprising a polymer addition system and a fluorometric method of detecting copper in the wastewater after the wastewater has been treated with polymer. A microfilter is used to separate the polymer-copper precipitate and other solids present from the wastewater stream. In this figure the sensor for detection of unreacted polymer is positioned in the wastewater stream at a point after the copper-polymer precipitate and other solids present have been removed from the wastewater. The signal from the fluorometer is used to control the distribution of treated wastewater in a feed forward manner the same as in FIG. 1.

FIG. 3 depicts copper detection and removal system 30. Copper detection and removal system 30 is the same as copper detection and removal system 11, except that sensor 34 is positioned in permeate stream 46, rather than in first tank 14. Sensor 34 is still designed to detect polymer, with the amount of polymer detected being used to control pump 28. With sensor 34 positioned at this point in the process, it is understood that any amount of polymer detected means that a gross excess of polymer is being added to first tank 14 and immediate appropriate corrective action should be taken in reducing the amount of polymer being added to first tank 14.

Figure 4:
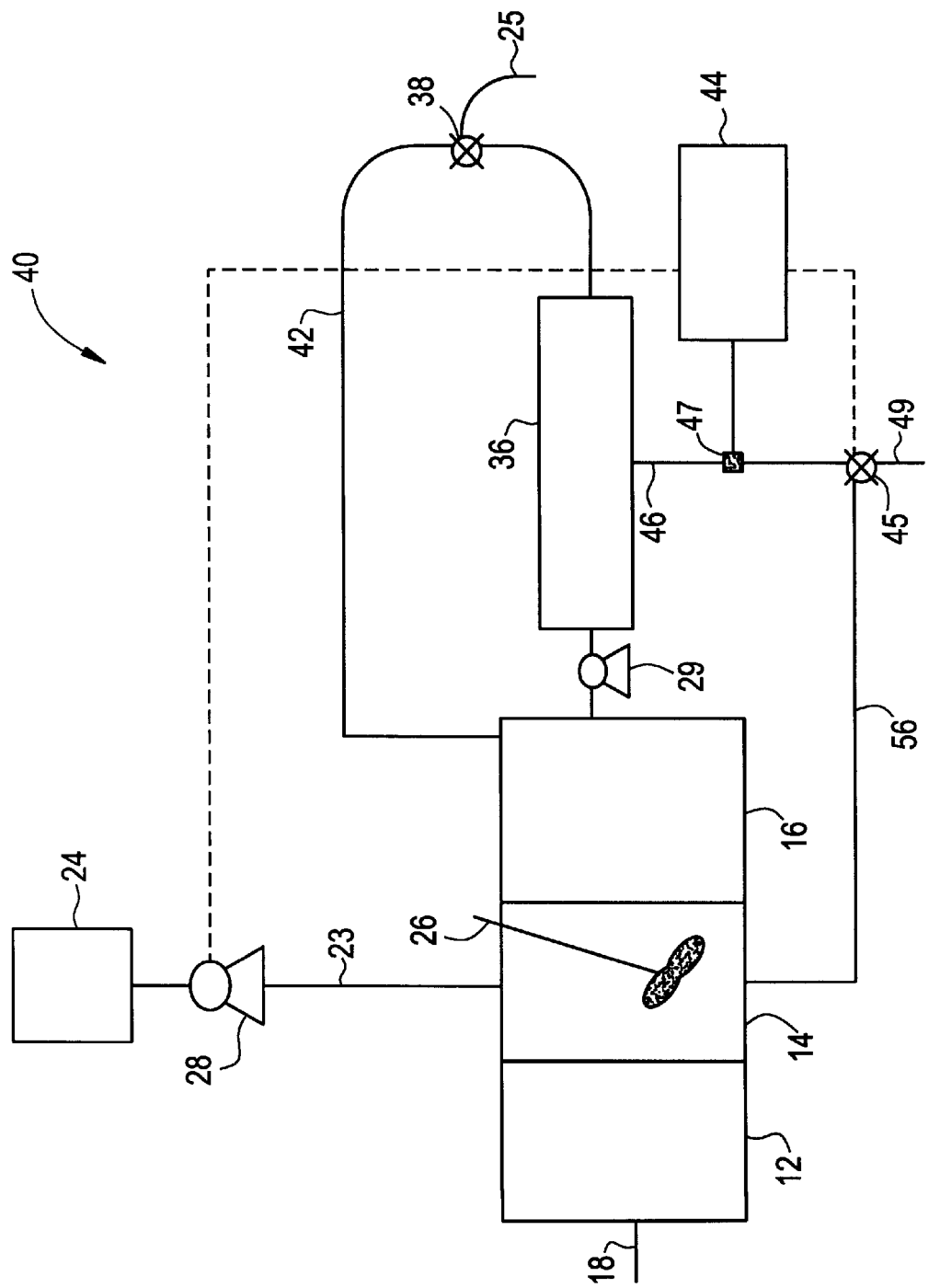
FIG. 4 depicts a wastewater treatment system comprising a polymer addition system and a fluorometric method of detecting copper in the wastewater after the wastewater has been treated with polymer. A microfilter is used to separate the polymer-copper precipitate and other solids present from the wastewater stream. In this figure there is a fluorometer used for fluorometric detection of copper located at a point after the precipitate of polymer-copper and other solids present have been removed from the wastewater. The signal from the fluorometer is used to control the amount of polymer added to the wastewater stream in a feedback manner and the signal is also used to control the distribution of treated wastewater in a feed forward manner the same as in FIG. 1.

FIG. 4 depicts copper detection and removal system 40. System 40 is the same as system 11 except for the fact that in system 40, there is no controller 32 or sensor 34 present, rather, the control of pump 28 is based directly on the signal coming from fluorometer 44. The signal coming from fluorometer 44 is directly related to the amount of copper still present in permeate stream 46; therefore, when copper is detected above the setpoint, the signal is not only used to increase the amount of polymer being added to first tank 14, it is also used to close valve 45.

Figure 5:
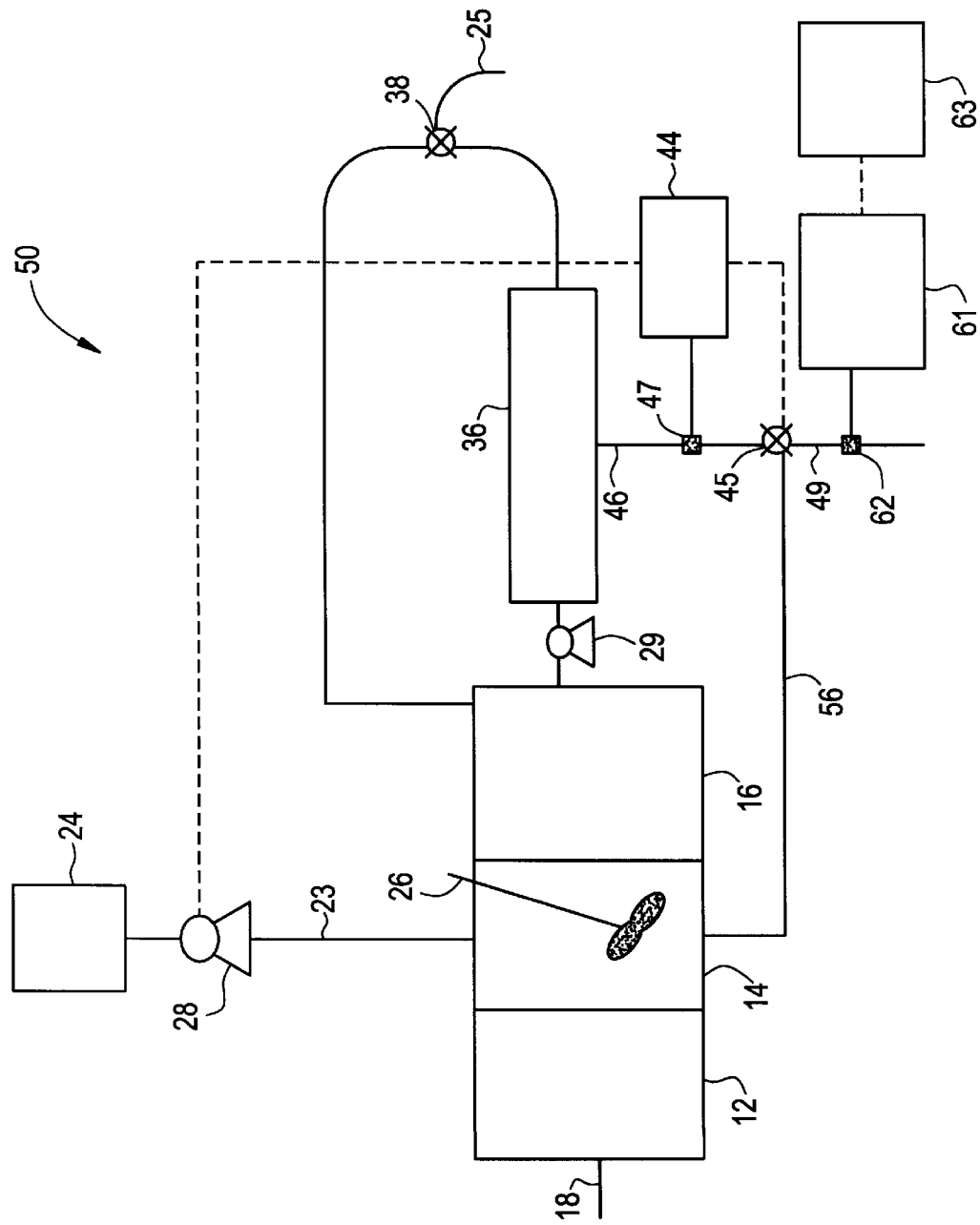
FIG. 5 depicts a wastewater treatment system comprising a polymer addition system and a fluorometric method of detecting copper in the wastewater after the wastewater has been treated with polymer. A microfilter is used to separate the polymer-copper precipitate and other solids present from the wastewater stream. In this figure there is a first fluorometer used for fluorometric detection of copper located at a point after the precipitate of polymer-copper and other solids present have been removed from the wastewater. The signal from the first fluorometer is used to control the amount of polymer added to the wastewater stream in a feedback manner. There is also a second fluorometer used to detect unreacted copper in that portion of the wastewater stream that is sent on for disposal. The signal from the first fluorometer is used to control the distribution of treated wastewater in a feed forward manner the same as in FIG. 1.

FIG. 5 depicts copper detection and removal system 50. As is true with system 40, in system 50, there is no controller 32 or sensor 34 present, rather, the control of pump 28 is based directly on the signal coming from fluorometer 44. The signal coming from fluorometer 44 is related to the amount of copper still present in permeate stream 46; therefore, when copper above the setpoint level is present, the signal is used to increase the amount of polymer being added to first tank 14. In addition to fluorometer 44, there is also present in system 50 a second fluorometer 61 with an optional datalogger 63 to continuously monitor the amount of copper present in the form of $Cu^{+2}$ ion in disposal line 49. Second fluorometer 61 detects copper by withdrawing a sample from disposal line 49 at sample point 62 and reacting said sample with a suitable reagent as described above.

Figure 6:
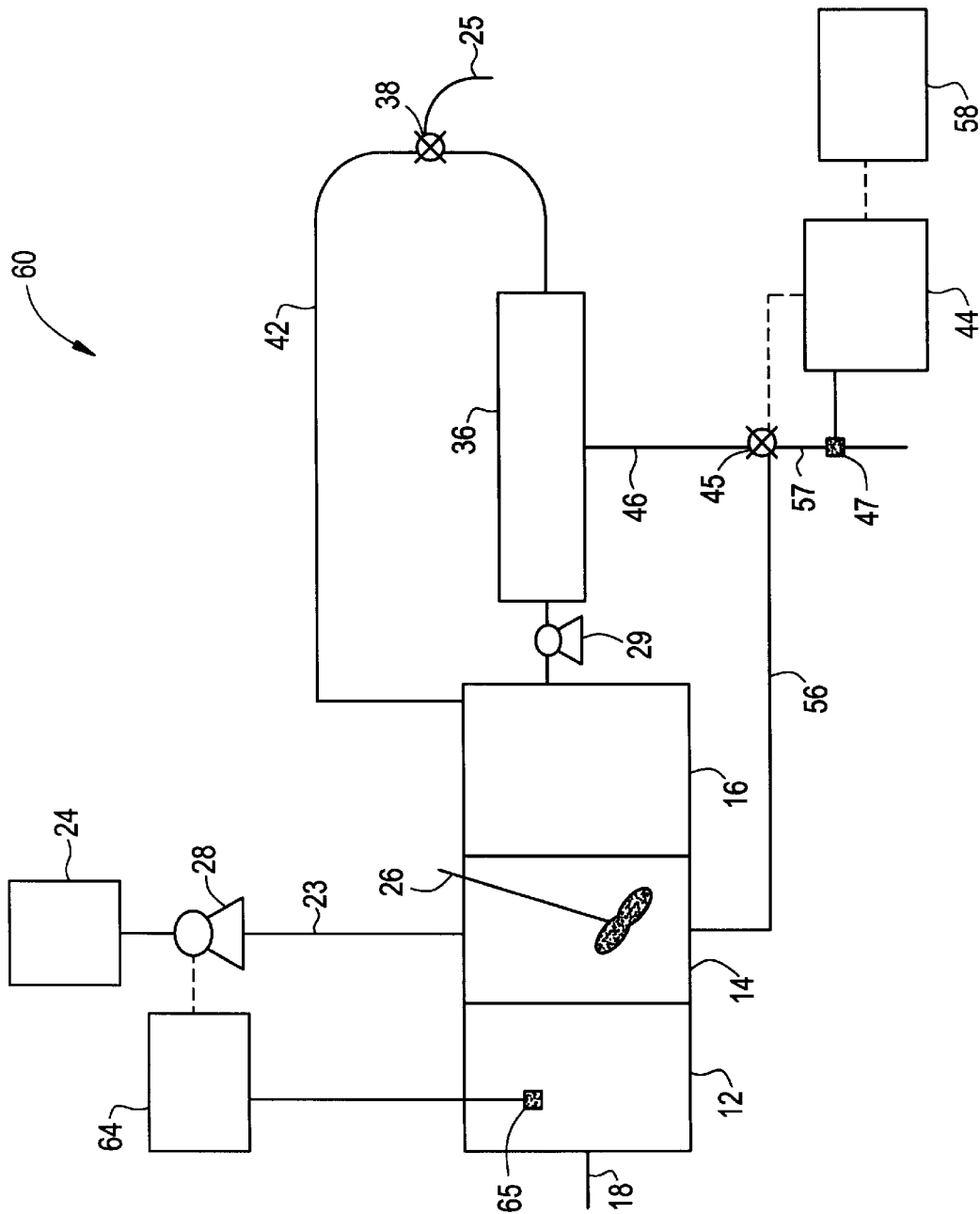
FIG. 6 depicts a wastewater treatment system comprising a polymer addition system and a fluorometric method of detecting copper in the wastewater after the wastewater has been treated with polymer. A microfilter is used to separate the polymer-copper precipitate and other solids present from the wastewater stream. In this figure there is first fluorometer used for fluorometric detection of copper located in the first tank of the three tank system used for addition and reaction of polymer. The signal from the first fluorometer is used to control the amount of polymer added to the wastewater stream in a feed forward manner. There is also a second fluorometer used to detect unreacted copper in that portion of the wastewater stream that is sent on for disposal. The signal from the second fluorometer is used to control the distribution of treated wastewater using feedback control.

FIG. 6 depicts copper detection and removal system 60. As is true with systems 40 and 50, in system 60, there is no controller 32 or sensor 34 present, rather, the control of pump 28 is based directly on the signal coming from fluorometer 64. Fluorometer 64 is positioned to detect copper in wastewater by using sample collector 65 to remove a sample from wastewater that is present in optional first tank 12. Thus, system 60 is an example of feed forward control, rather than the feedback control present in the previous systems. Fluorometer 44 is also present in system 60 for monitoring of copper in final drain line 57. As is the case with previous systems, the signal from fluorometer 44 is used to control drain valve 45. Should the amount of copper detected exceed specifications, then permeate in line 46 can be recirculated through recirculation line 56 back to first tank 14 for further treatment with polymer. This recirculation can be done automatically by having a signal from fluorometer 44 used to control drain valve 45. This would work as follows: the normal position of drain valve 45 is open, however when the copper level is found by fluorometric analysis to be past an acceptable setpoint, then the signal from fluorometer 44 is used to close drain valve 45 which causes wastewater to recirculate back to first tank 14 for further treatment with polymer. Optional datalogger 58 can be used to keep a continuous record of fluorescence detected so that the overall removal process can be constantly monitored.

Figure 7:
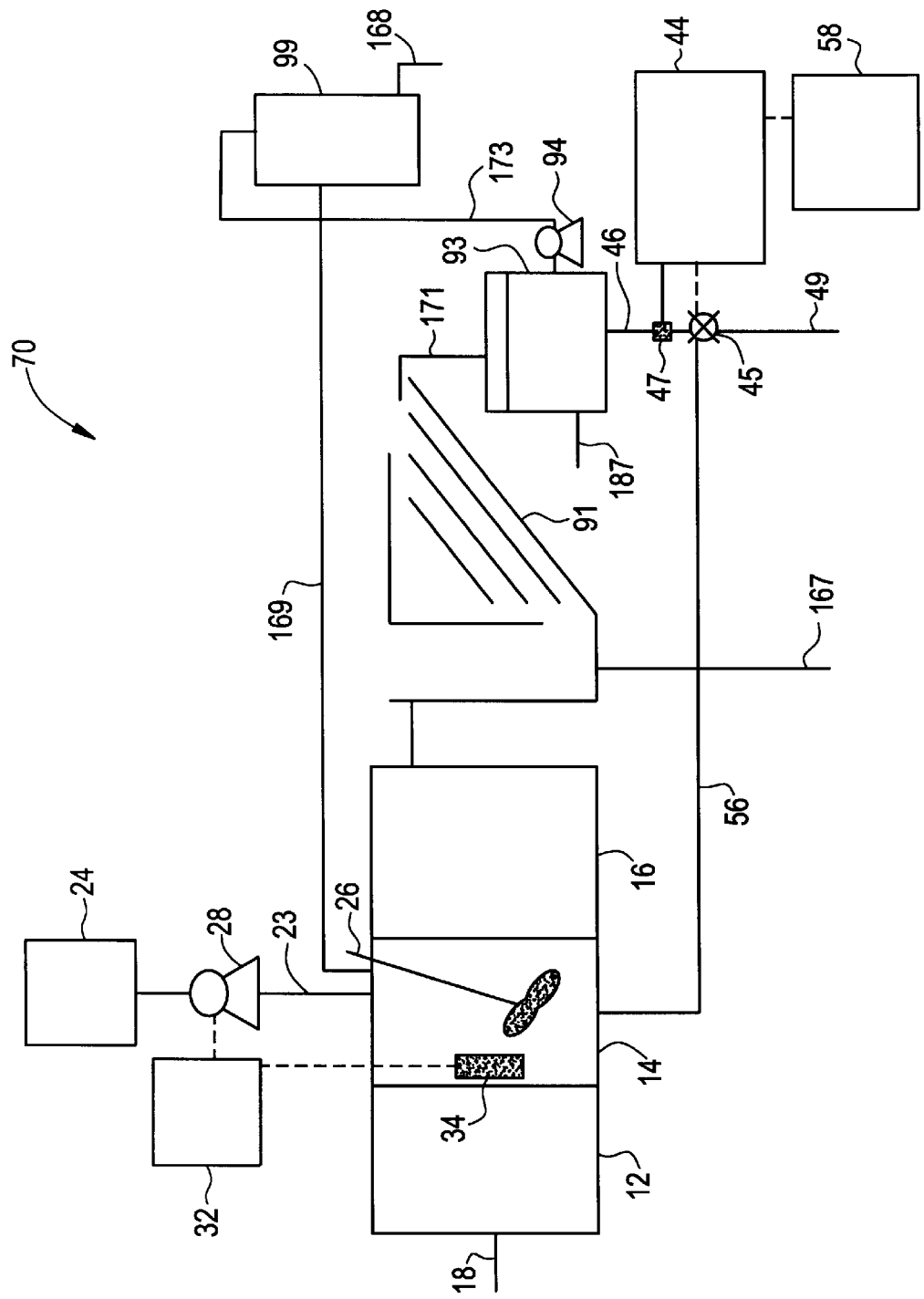
FIG. 7 is the same as FIG. 1A except that a lamellar clarifier followed by a sand filter and back wash tank is used in place of the microfilter.

FIG. 7 depicts copper detection and removal system 70. This is the same as copper detection and removal system 11, except that the microfilter in system 10 has been replaced by lamellar clarifier 91, sand filter 93 and back wash tank 99 for separation of precipitate from wastewater. After separation in the lamellar clarifier 91 solids are sent through sludge line 167 for further dewatering using conventional dewatering equipment, not depicted. The effluent water, which still contains some solids is conveyed from lamellar clarifier 91 to sand filter 93 through transfer line 171. Further separation takes place in sand filter 93 from which water leaves through permeate line 46. Periodically, sand filter 93 is cleaned by running fresh water through line 187 into the filter causing solids and water to be displaced from the filter through transfer line 173, using pump 94 to enter back wash tank 99. From back wash tank 99 solids leave through sludge line 168 and water is recycled through line 169 back to first tank 14 for further treatment.

Figure 7A:
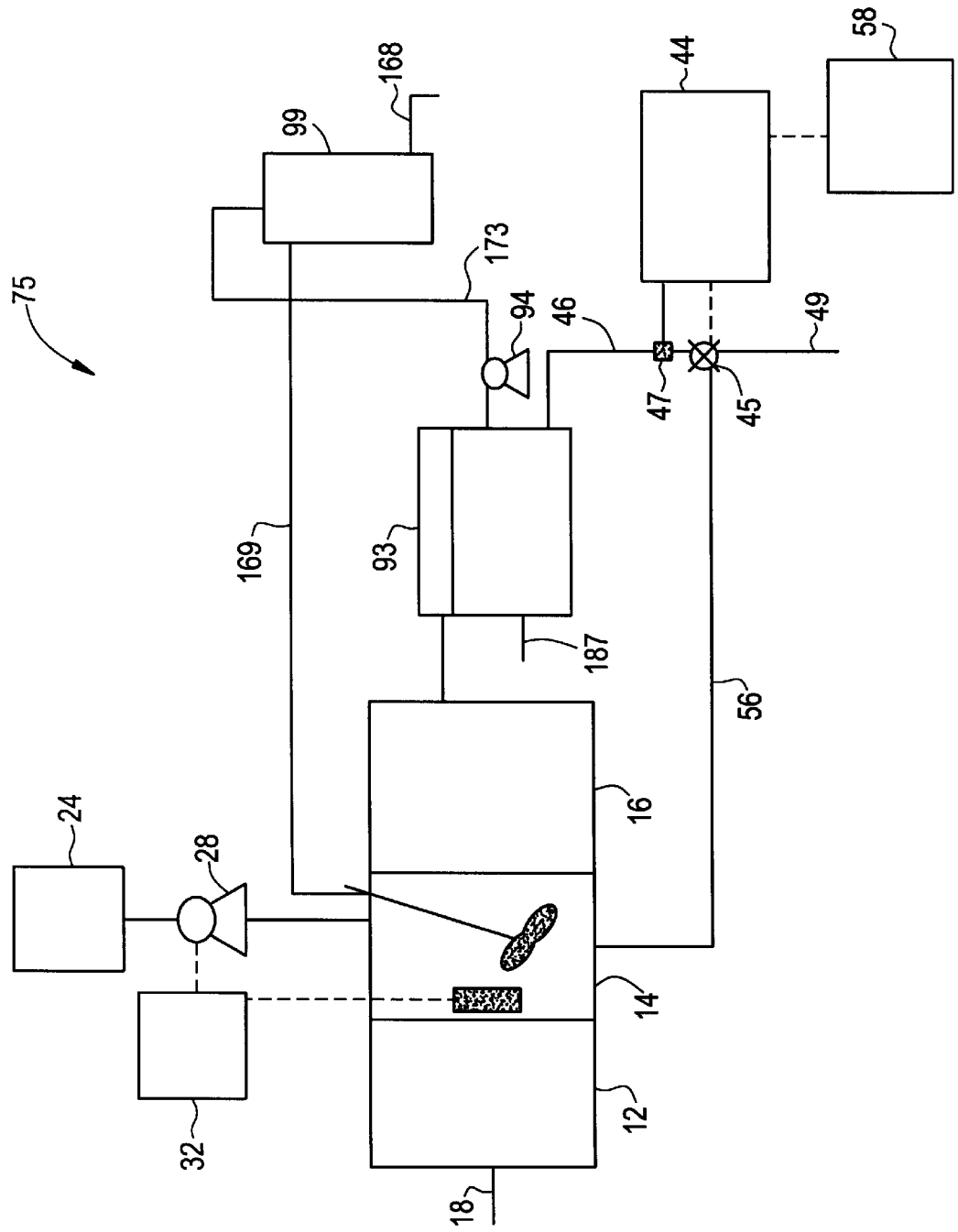
FIG. 7A is the same as FIG. 1A except that a sand filter followed by a back wash tank is used in place of the microfilter.

FIG. 7A depicts copper detection and removal system 75. This is the same as copper detection and removal system 11, except that the microfilter in system 10 has been replaced by a sand filter 93 which is used in conjunction with back wash tank 99 for separation of precipitate from wastewater. After separation, from back wash tank 99 precipitate leaves through sludge line 168 and water is recycled through line 169 back to first tank 14 for further treatment. Precipitate leaving through sludge line 168 is sent for further dewatering using conventional dewatering equipment, not depicted.

Figure 8A:
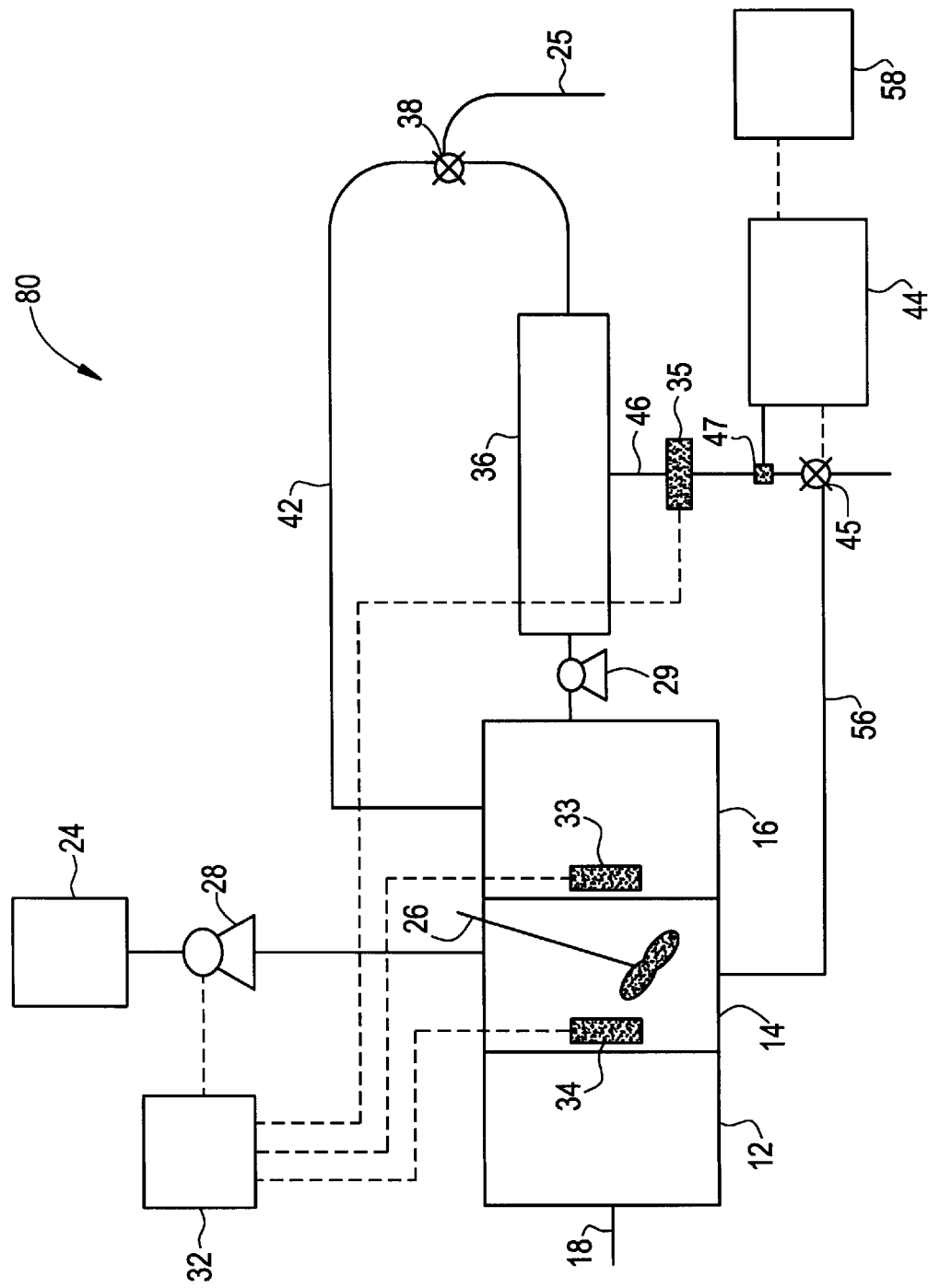
FIG. 8A is the same as FIG. 1A except that a second sensor for unreacted polymer is used in the third tank of the 3-tank polymer addition and reaction tank system, and a third sensor for unreacted polymer is positioned after the wastewater stream has been through the microfilter. All three sensors are connected to the controller used to determine the amount of polymer added to the wastewater stream.

FIG. 8A depicts copper detection and removal system 80. This is the same as copper detection and removal system 11, with the addition of another polymer sensor 33 located in second tank 16 and another polymer sensor 35 located in permeate stream 46. All sensors are connected to controller 32 which uses their signals to determine the optimal flow rate for pump 28 to pump polymer into first tank 14.

FIG. 8B depicts copper detection and removal system 83. This is the same as copper detection and removal system 11, with the addition of another polymer sensor 33 located in second tank 16. Both sensors are connected to controller 32 which uses their signals to determine the optimal flow rate for pump 28 to pump polymer into first tank 14.

Figure 8C:
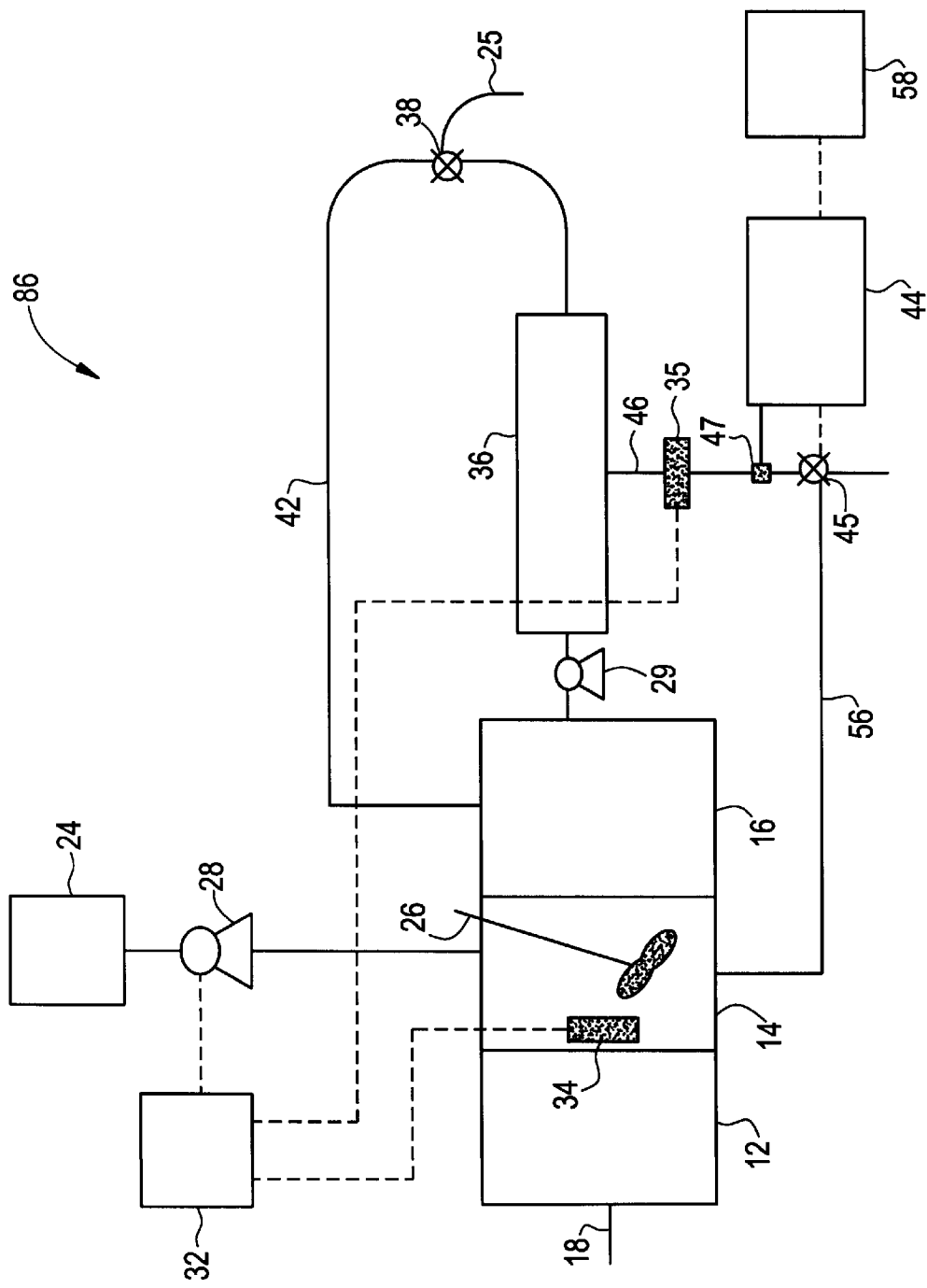
FIG. 8C is the same as FIG. 1A except that a second sensor for unreacted polymer is positioned in the permeate line from the microfilter. Both sensors are connected to the controller used to determine the amount of polymer added to the wastewater stream.

FIG. 8C depicts copper detection and removal system 86. This is the same as copper detection and removal system 11, with the addition of another polymer sensor 35 located in permeate stream 46. Both sensors are connected to controller 32 which uses their signals to determine the optimal flow rate for pump 28 to pump polymer into first tank 14.

Figure 9:
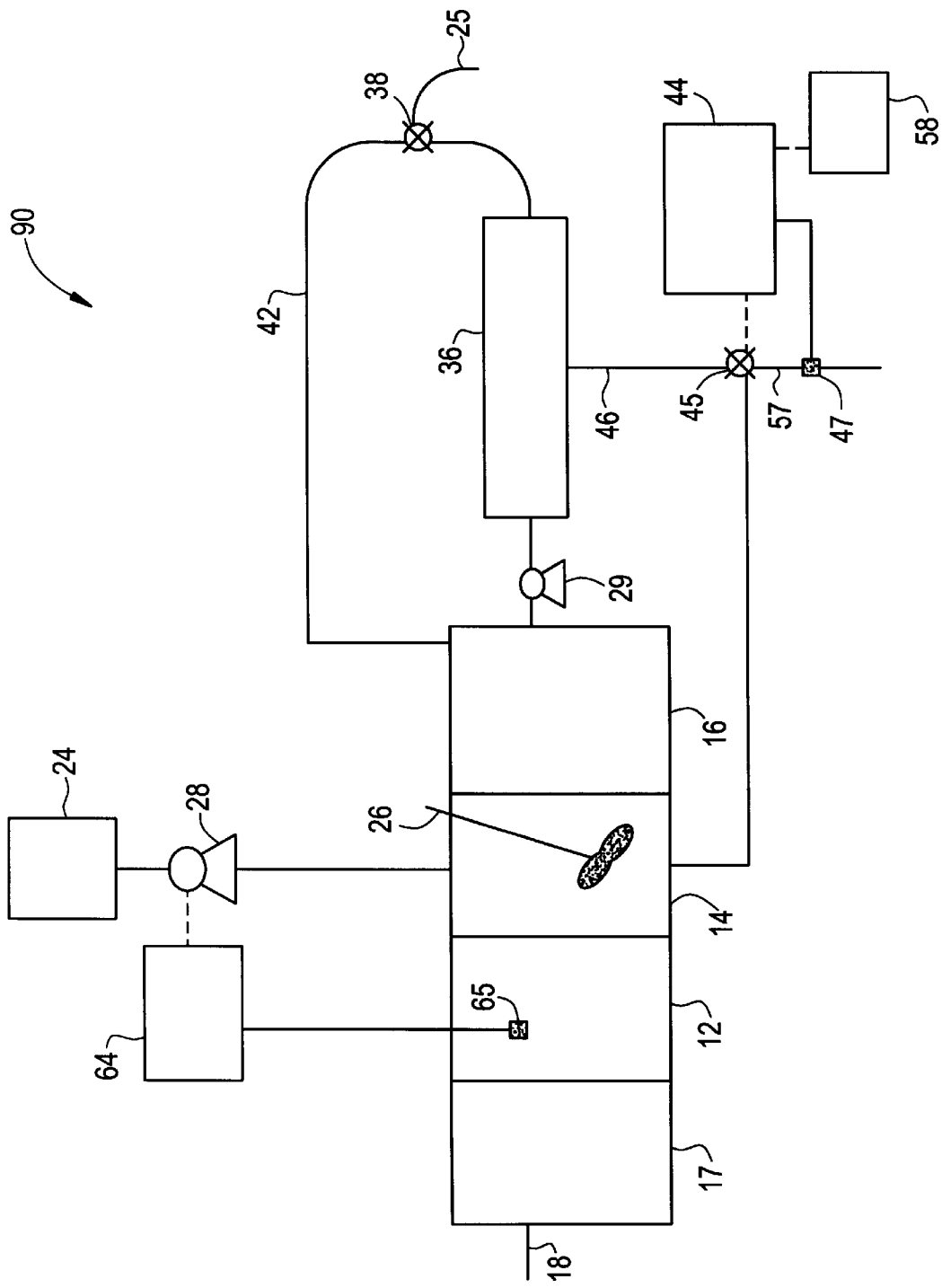
FIG. 9 is the same as FIG. 6 with the addition of a fourth tank to the polymer addition-reaction tank system. The purpose of the fourth tank is to allow for the equalization of the wastewater prior to the addition of the polymer.

FIG. 9 depicts copper detection and removal system 90. This is the same as copper detection and removal system 60, except that a fourth tank 17 is present. Fourth tank 17 is positioned such that wastewater enters it prior to entering optional first tank 12. In fourth tank 17 wastewater enters and is equalized by allowing the wastewater to accumulate long enough in the tank such that the wastewater assumes an even consistency (in terms of percent solids) prior to leaving fourth tank 17. Equalization takes place from 20 minutes to about 2 hours with the preferred amount of time being about 40 minutes. This equalization of wastewater, by evening out the consistency of the solids within the wastewater, facilitates the detection and removal of copper in the remainder of the system.

Figure 10:
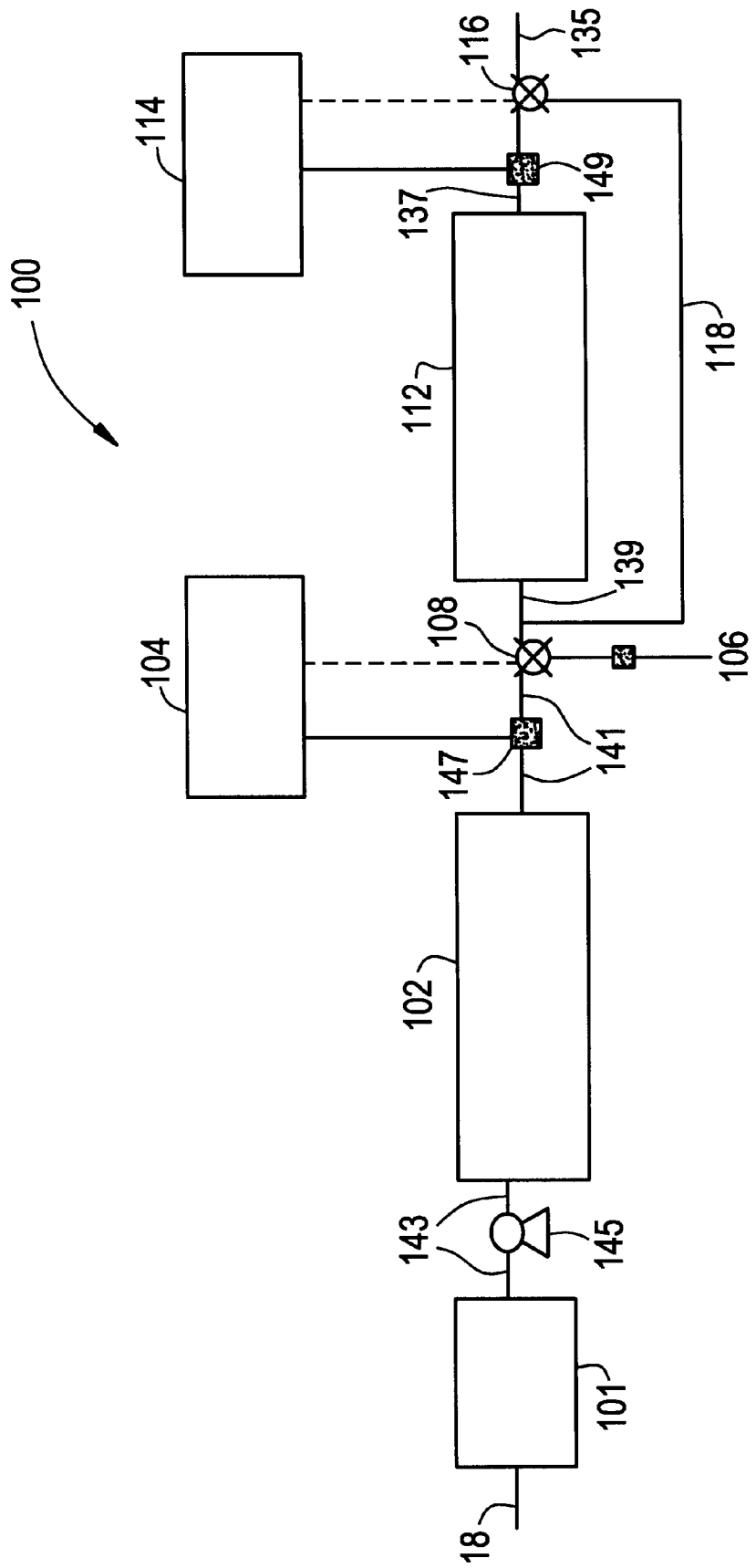
FIG. 10 depicts a system for detection and removal of copper from a semiconductor wastewater process stream wherein an ion exchange column is used to remove copper from the wastewater and a fluorometer is used to detect copper in the exit line from the ion exchange column. A second ion exchange column with a second fluorometer can be optionally included. As with previous embodiments, the signal from the fluorometer is used to control a valve that in the event acceptable levels of copper are detected will send the treated wastewater for disposal and in the event unacceptable levels of copper are detected will send the treated wastewater either to a second ion-exchange column for further treatment or will recycle the treated wastewater back to the first ion-exchange column for further treatment.

FIG. 10 depicts copper detection and removal system 100. In this system, wastewater enters through inlet line 18 into sole tank 101 where the pH of wastewater is adjusted using an appropriate reagent, previously described, such that wastewater leaves sole tank 101 with a pH of from about 5 to about 10. From sole tank 101, wastewater is pumped by pump 145 through transfer line 143 to enter first ion exchange column 102 where some of the copper is removed. First fluorometer 104 is positioned to detect copper at sample point 147 located in exit line 141 from first ion exchange column 102. If the wastewater coming out of first ion exchange column 102 has had enough copper removed so that it meets the setpoint, determined by environmental regulations, then this cleaned wastewater may be sent directly on to drainport 106 by opening drain valve 108. As in previous embodiments, the signal from first fluorometer 104 is used to open and close drain valve 108. In the event that further removal of copper is required then drain valve 108 is closed and wastewater is conveyed in transfer line 139 to optional second ion exchange column 112 which can be used to remove more copper from wastewater. Optional second fluorometer 114 can be used to detect copper in transfer line 137 at sample point 149. The signal from optional second fluorometer 114 can be used to open and close second drain valve 116 in the similar way that the signal from first fluorometer 104 is used to open and close drain valve 108. Wastewater that still does not meet specifications for levels of copper after contact with optional second ion exchange column 112 can be recycled back through the process through recycle line 118. Wastewater that does meet copper specification is sent for disposal through transfer line 135.

Figure 10A:
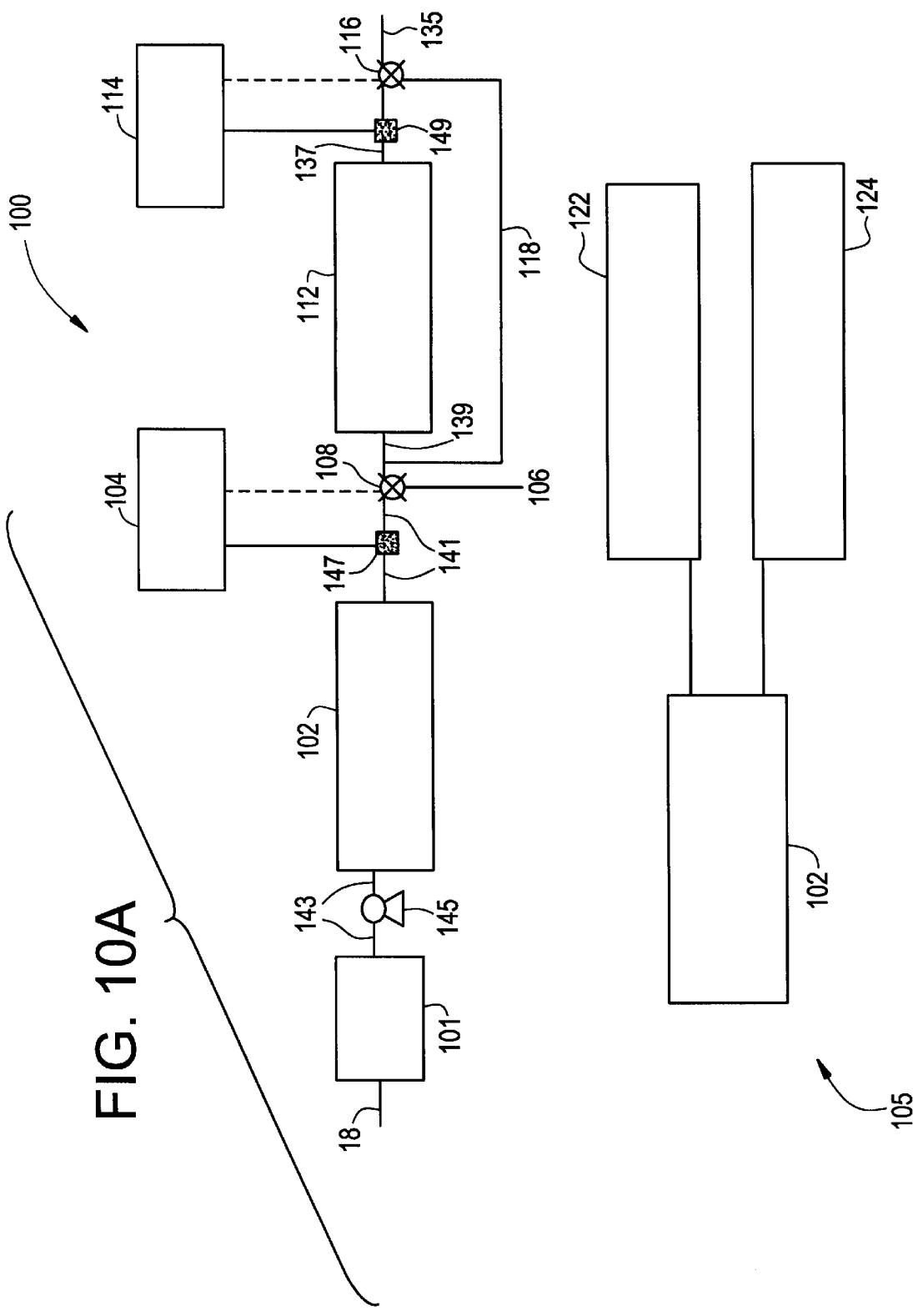
FIG. 10A is the same as FIG. 10 with the addition of a resin regeneration step in which said ion exchange column is regenerated using standard acidic treatment with either electrowinning or resource recovery of the copper being the next step.

FIG. 10A depicts copper detection and removal system 100, previously described, and resin regeneration, with optional recovery of copper, system 105. Resin regeneration with optional recovery of copper system 105 shows the regeneration of ion exchange column with acid followed either by electrowinning 122 or copper recovery 124. Both electrowinning and copper recovery can be done using standard techniques known in the art. Electrowinning is an electrolytic process in which metal ions are reduced at a cathode to the elemental state; in this case copper ions are reduced to copper metal and plated onto an inert (usually stainless steel) electrode. The copper deposit is mechanically stripped from the cathode with a knife or a chisel and can be sold for reuse.

Figure 11:
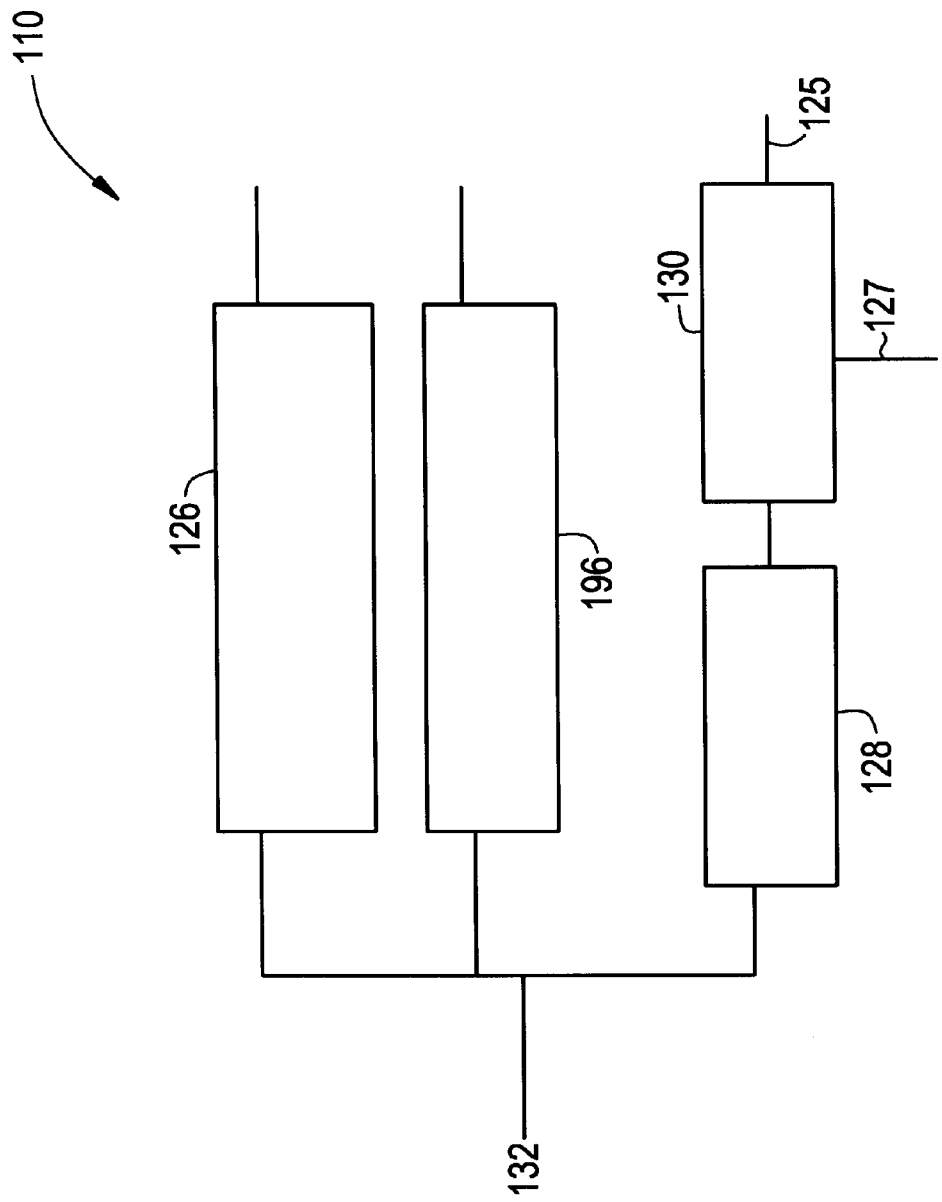
FIG. 11 depicts treatment of the dewatered sludge containing the precipitate of copper and polymer. The first treatment involves recovery of the copper metal using either hydrometallurgical processing or thermal processing and the second treatment option involves treatment of the sludge using a drier and a cementation process prior to disposal in an approved landfill.

FIG. 11 depicts treatment system 110 for recovery of copper metal and/or treatment and disposal of sludge material. Recovery of copper metal takes place in hydrometallurgical process 126 or thermal process 196. In hydrometallurgical process 126, the solids(metals) are selectively dissolved and reprecipitated using techniques known in the art. In thermal process 196, high temperatures are used to separate the copper from the rest of the sludge.

Treatment of sludge material, without removing metal, takes place by first drying the sludge in sludge drier 128 and then subjecting the dried sludge to a cementation process in equipment 130. Cementation is a process used to stabilize sludge and prevent the leaching of heavy metals from the landfilled sludge. Typically, lime or silicaeous (e.g., sodium silicate) materials are mixed with the sludge, as illustrated in FIG. 11 wherein lime or silacaeous materials are added to dried sludge in line 127. The stabilized sludge leaves equipment 130 in line 125 and is qualified for landfilling based on passing a leachability test and is disposed of in full compliance with all local and national laws.

By using the embodiments of the present invention it is possible to reduce the amount of copper in wastewater from a semiconductor process or a printed circuit board process by between about 1% and about 99%. This makes the claimed invention of great value in the semiconductor and printed circuit board industry.

While the present invention is described above in connection with preferred or illustrative embodiments, these embodiments are not intended to be exhaustive or limiting of the invention. It is to be understood that various changes and modifications to the presently preferred embodiments described herein will be apparent to those skilled in the art. Such changes and modifications may be made without departing from the spirit and scope of the present invention and without diminishing its attendant advantages. The invention is intended to cover all alternatives, changes, modifications and equivalents included within its spirit and scope, as defined by the appended claims.

What is claimed is:

1. A system to detect and remove copper from wastewater streams in the manufacture of semiconductors comprising:
    a) a fluorometer;
    b) a suitable fluorometric reagent that when added to the wastewater reacts with any copper present in the form of $Cu^{+2}$ ion to form a reagent-$Cu^{+2}$ complex;
    c) a polymer, which when added to the wastewater stream causes the precipitation of any copper present in the form of $Cu^{+2}$ ion;
    d) a polymer distribution and reaction component comprising
        i) a means to add polymer to the wastewater,
        ii) a controller to regulate the flow of polymer into the wastewater, and
        iii) at least two tanks;
    e) at least one sensor to detect unreacted polymer;
    f) a means to separate the precipitate from the wastewater stream;
    g) a fluorometric controller which uses the signal from said fluorometer to control a valve that determines whether the wastewater stream is discharged or recycled for further treatment;
    h) optionally, a reagent to adjust pH of wastewater prior to it being contacted with polymer; and
    i) optionally, at least one tank to hold the wastewater while its pH is being adjusted; and
    j) optionally, at least one tank to hold the wastewater while it is being equalized, prior to its pH being adjusted.

2. The system of claim 1 further comprising:
    an additional fluorometer positioned to test a sample at a different place in the process compared to the fluorometer of section a).

3. The system of claim 1 further comprising:
    k) one additional sensor to detect unreacted polymer, positioned in a different place than the sensor described in section e).

4. The system of claim 3 further comprising:
    l) a second additional sensor to detect unreacted polymer, positioned in a different place than the sensor described in section e) and the additional sensor described in section k).

5. A system to detect and remove copper from wastewater streams in the manufacture of printed circuit boards comprising:
    a) a fluorometer;
    b) a suitable fluorometric reagent that when added to the wastewater reacts with any copper present in the form of $Cu^{+2}$ ion to form a reagent-$Cu^{+2}$ complex;

c) a polymer, which when added to the wastewater stream causes the precipitation of any copper present in the form of $Cu^{+2}$ ion;
d) a polymer distribution and reaction component comprising
   i) a means to add polymer to the wastewater,
   ii) a controller to regulate the flow of polymer into the wastewater, and
   iii) at least two tanks;
e) at least one sensor to detect unreacted polymer;
f) a means to separate the precipitate from the wastewater stream;
g) a fluorometric controller which uses the signal from said fluorometer to control a valve that determines whether the wastewater stream is discharged or recycled for further treatment;
h) optionally, a reagent to adjust pH of wastewater prior to it being contacted with polymer;
i) optionally, at least one tank to hold the wastewater while its pH is being adjusted; and
j) optionally, at least one tank to hold the wastewater while it is being equalized, prior to its pH being adjusted.

6. The system of claim 5 further comprising:
an additional fluorometer positioned to test a sample at a different place in the process compared to the fluorometer of section a).

7. The system of claim 5 further comprising:
k) one additional sensor to detect unreacted polymer, positioned in a different place than the sensor described in section e).

8. The system of claim 7 further comprising:
l) a second additional sensor to detect unreacted polymer, positioned in a different place than the sensor described in section e) and the additional sensor described in section k).

9. A method to detect and remove copper from wastewater streams from semiconductor processes comprising:
(i) providing a fluorometer and;
(ii) providing a suitable fluorometric reagent for copper;
(iii) providing a polymer capable of reacting with copper in the form of $Cu^{+2}$ ion to form a precipitate;
(iv) providing at least one wastewater stream from said semiconductor processes, with the pH of said wastewater stream being between about 5 and about 10;
(v) contacting said wastewater with said polymer capable of reacting with said copper to form a precipitate;
(vi) removing said precipitate from said wastewater to form a permeate stream;
(vii) adding said suitable fluorometric reagent for copper to a sample of said permeate stream to form a reagent-$Cu^{+2}$ moiety;
(viii) using said fluorometer to measure the fluorescent signal of the reagent-$Cu^{+2}$ moiety;
(ix) determining the amount of copper present in said permeate stream from said fluorescent signal; and
(x) using said amount of copper present to
   (a) adjust the control of the feed rate of said polymer to said wastewater stream; and
   (b) control a valve that determines whether the wastewater stream is discharged or recycled for further treatment.

10. A method to detect and remove copper from wastewater streams from printed circuit board processes comprising:
(i) providing a fluorometer and;
(ii) providing a suitable fluorometric reagent for copper;
(iii) providing a polymer capable of reacting with copper in the form of $Cu^{+2}$ ion to form a precipitate;
(iv) providing at least one wastewater stream from said semiconductor processes, with the pH of said wastewater stream being between about 5 and about 10;
(v) contacting said wastewater with said polymer capable of reacting with said copper to form a precipitate;
(vi) removing said precipitate from said wastewater to form a permeate stream;
(vii) adding said suitable fluorometric reagent for copper to a sample of said permeate stream to form a reagent-$Cu^{+2}$ moiety;
(viii) using said fluorometer to measure the fluorescent signal of the reagent-$Cu^{+2}$ moiety;
(ix) determining the amount of copper present in said permeate stream from said fluorescent signal; and
(x) using said amount of copper present to
   (a) adjust the control of the feed rate of said polymer to said wastewater stream; and
   (b) control a valve that determines whether the permeate stream is discharged or recycled for further treatment.

11. A system to detect and remove copper from wastewater streams in the manufacture of semiconductors comprising:
a) a fluorometer;
b) a suitable fluorometric reagent that when added to the wastewater reacts with any copper present in the form of $Cu^{+2}$ ion to form a reagent-$Cu^{+2}$ complex;
c) at least one ion exchange column;
d) a fluorometric controller which uses the signal from said fluorometer to control a valve that determines whether the wastewater stream is discharged or recycled for further treatment; and
e) optionally, a tank to contain the wastewater when it is being equalized.

12. A system to detect and remove copper from wastewater streams in the manufacture of printed circuit boards comprising:
a) a fluorometer;
b) a suitable fluorometric reagent that when added to the wastewater reacts with any copper present in the form of $Cu^{+2}$ ion to form a reagent-$Cu^{+2}$ complex;
c) at least one ion exchange column;
d) a fluorometric controller which uses the signal from said fluorometer to control a valve that determines whether the wastewater stream is discharged or recycled for further treatment; and
e) optionally, a tank to contain the wastewater when it is being equalized.

13. A method to detect and remove copper from wastewater streams from semiconductor processes comprising:
(i) providing a fluorometer;
(ii) providing a suitable fluorometric reagent for copper;
(iii) providing at least one wastewater stream from said semiconductor processes, with the pH of said wastewater stream being between about 5 and about 10;
(iv) providing at least one ion exchange column;
(v) passing said at least one wastewater stream through said at least one ion exchange column;
(vi) adding said suitable fluorometric reagent to a sample of said wastewater stream after it has passed through said at least one ion exchange column;

(vii) using said fluorometer to measure the fluorescent signal of reagent-$Cu^{+2}$ moiety;

(viii) determining the amount of copper present in said wastewater stream after it has passed through said at least one ion exchange column;

(ix) using said amount of copper present to control a valve that determines whether the wastewater stream is discharged or recycled for further treatment.

14. A method to detect and remove copper from wastewater streams from printed circuit board processes comprising:

(i) providing a fluorometer;

(ii) providing a suitable fluorometric reagent for copper;

(iii) providing at least one wastewater stream from said printed circuit board processes, with the pH of said wastewater stream being between about 5 and about 10;

(iv) providing at least one ion exchange column;

(v) passing said at least one wastewater stream through said at least one ion exchange column;

(vi) adding said suitable fluorometric reagent to a sample of said wastewater stream after it has passed through said at least one ion exchange column;

(vii) using said fluorometer to measure the fluorescent signal of reagent-$Cu^{+2}$ moiety;

(viii) determining the amount of copper present in said wastewater stream after it has passed through said at least one ion exchange column;

(ix) using said amount of copper present to control a valve that determines whether the wastewater stream is discharged or recycled for further treatment.

* * * * *